US012781183B2

(12) United States Patent
Janzen et al.

(10) Patent No.: US 12,781,183 B2
(45) Date of Patent: Nov. 3, 2026

(54) LACTIC ACID BACTERIAL STRAINS WITH IMPROVED TEXTURIZING PROPERTIES

(71) Applicant: Chr. Hansen A/S, Hoersholm (DK)

(72) Inventors: Thomas Janzen, Hoersholm (DK); Ditte Christiansen, Hoersholm (DK); Jesper Broend, Hoersholm (DK); Victoria Prebner, Hoersholm (DK); Ilenia Manuguerra, Hoersholm (DK); Geoffrey Ras, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 339 days.

(21) Appl. No.: 18/260,850

(22) PCT Filed: Jan. 6, 2022

(86) PCT No.: PCT/EP2022/050208
§ 371 (c)(1),
(2) Date: Jul. 10, 2023

(87) PCT Pub. No.: WO2022/152615
PCT Pub. Date: Jul. 21, 2022

(65) Prior Publication Data

US 2024/0166989 A1 May 23, 2024

(30) Foreign Application Priority Data

Jan. 12, 2021 (EP) .................................... 21151176

(51) Int. Cl.

| | |
|---|---|
| ***C12N 1/20*** | (2026.01) |
| ***A23C 9/123*** | (2006.01) |
| ***A23C 11/10*** | (2021.01) |
| ***C12N 1/205*** | (2026.01) |
| ***C12N 9/12*** | (2006.01) |
| *C12R 1/225* | (2006.01) |
| *C12R 1/46* | (2006.01) |

(52) U.S. Cl.
CPC ............ *C12N 1/205* (2021.05); *A23C 9/1238* (2013.01); *A23C 11/10* (2013.01); *A23C 11/106* (2013.01); *C12N 9/12* (2013.01); *C12N 9/1205* (2013.01); *C12Y 207/01006* (2013.01); *C12Y 207/13003* (2013.01); *A23V 2400/123* (2023.08); *A23V 2400/249* (2023.08); *C12R 2001/225* (2021.05); *C12R 2001/46* (2021.05)

(58) Field of Classification Search
CPC ........ C12N 1/205; C12N 9/12; C12N 9/1205; A23C 9/1238; A23C 11/10; A23C 11/106; C12Y 207/01006; C12Y 207/13003; C12R 2001/225; C12R 2001/46; A23V 2400/123; A23V 2400/249
USPC ............................................................ 426/18
See application file for complete search history.

(56) References Cited

PUBLICATIONS

De Vin et al., Molecular and biochemical analysis of the galactose phenotype of dairy *Streptococcus thermophilus* strains reveals four different fermentation profiles (Year: 2005).*

(Continued)

*Primary Examiner* — Brent T O'Hern
(74) *Attorney, Agent, or Firm* — Yoshimi D. Barron

(57) ABSTRACT

The present invention relates to a novel *Streptococcus thermophilus* strain having improved texturizing properties, compositions comprising said strain as well as fermented products manufactured using said strain.

6 Claims, 5 Drawing Sheets

Specification includes a Sequence Listing.

```
DSM 33118     AAAATATTGATTTTCCATGTGAAAGGGGTTACAATTTCAGTATAAACAAAAAGAATAAGTGAGATACATC
Mother strain AAAATATTGATTTTCCATGTGAAAGGGGTTACGATTTCAGTATAAACAAAAAGAATAAGTGAGATACATC
AY704368      AAAATATTGATTTTCCATGTGAAAGGGGTTACGATTTCAGTATAAACAAAAAGAATAAGTGAGATACATC
Consensus     AAAATATTGATTTTCCATGTGAAAGGGGTTACGATTTCAGTATAAACAAAAAGAATAAGTGAGATACATC
                     -35                      -10                        RBS
```

(56) References Cited

PUBLICATIONS

Alexandraki, Voula et al.; "Comparative Genomics of *Streptococcus thermophilus* Support Important Traits Concerning the Evolution, Biology and Technological Properties of the Species"; Frontiers in Microbiology, vol. 10; Dec. 20, 2019; 24 pages.

De Vin, Filip et al.; "Molecular and Biochemical Analysis of the Galactose Phenotype of Dairy *Streptococcus thermophilus* Strains Reveals Four Different Fermentation Profiles"; Applied and Environmental Microbiology, vol. 71, No. 7; Jul. 2005; pp. 3659-3667.

Hu, Tong et al.; "Technological properties assessment and two component systems distribution of *Streptococcus thermophilus* strains isolated from fermented milk"; Archives of Microbiology, vol. 200; Dec. 13, 2017; 25 pages.

Robitaille, G. et al.; "Fat-free yogurt made using a galactose-positive exopolysaccharide-producing recombinant strain of *Streptococcus thermophilus*"; J. Dairy Sci., vol. 92, No. 2; Feb. 1, 2009; pp. 477-482.

Thevenard, B. et al.; "Response of *S. thermophilus* LMD-9 to bacitracin: Involvement of a BceRS/AB-like module and of the rhamnose-glucose polysaccharide synthesis pathway"; International Journal of Food Microbiology, vol. 177; Feb. 22, 2014; pp. 89-97.

UNIPROT Consortium; Full=Histidine kinase HPK7; https://www.uniprot.org/uniprot/A0A2H4K9M7.txt?version=9; Dec. 2020; 1 page.

Vaillancourt, Katy et al.; "Characterization of a Galactokinase-Positive Recombinant Strain of *Streptococcus thermophilus*"; Applied and Environmental Microbiology, vol. 70, No. 8; Aug. 2004; pp. 4596-4603.

Xiong, Zhi-Qiang et al.; "Comparison of gal-lac operons in wild-type galactose-positive and -negative *Streptococcus thermophilus* by genomics and transcription analysis"; Journal of Industrial Microbiology & Biotechnology, vol. 46, No. 5; Feb. 4, 2019; pp. 751-758.

* cited by examiner

| | |
|---|---|
| DSM 33118 | AAAATA**TTGATT**TTCCATGTGAAAGGGGT**TACAAT**TTCAGTATAAACAAAAAGAATAAGT**GAGA**TACATC |
| Mother strain | AAAATA**TTGATT**TTCCATGTGAAAGGGGT**TACGAT**TTCAGTATAAACAAAAAGAATAAGT**GAGA**TACATC |
| AY704368 | AAAATA**TTGATT**TTCCATGTGAAAGGGGT**TACGAT**TTCAGTATAAACAAAAAGAATAAGT**GAGA**TACATC |
| Consensus | AAAATA**TTGATT**TTCCATGTGAAAGGGGT**TACGAT**TTCAGTATAAACAAAAAGAATAAGT**GAGA**TACATC |
| | -35 (TTGATT); -10 (TACGAT); RBS (GAGA) |

Figure 1

LACTIC ACID BACTERIAL STRAINS WITH IMPROVED TEXTURIZING PROPERTIES

CROSS-REFERENCE TO RELATED APPLICATIONS

The present application is the U.S. National Stage of International Application No. PCT/EP2022/050208, filed Jan. 6, 2022, and claims priority to European Patent Application No. 21151176.1, filed Jan. 12, 2021.

SEQUENCE LISTING

The instant application contains a Sequence Listing submitted electronically in ASCII format incorporated by reference herein in its entirety. Said ASCII file, created on Jan. 9, 2024, is named "030427_0397_SL_20240109.txt" and is 17 kilobytes in size.

TECHNICAL FIELD OF THE INVENTION

The present invention relates to mutants of *Streptococcus thermophilus*, which were found to have improved texturizing properties while maintaining the growth properties of its parent strain. The present invention, furthermore, relates to compositions, such as a starter culture, comprising one or more of these mutants and to fermented products made using these mutants.

BACKGROUND OF THE INVENTION

The food industry uses numerous bacteria, in particular lactic acid bacteria, in order to improve the texture of food. In the dairy industry, lactic acid bacteria are used intensively in order to bring about the acidification of milk (by fermentation) but also in order to texturize the product into which they are incorporated.

Among the lactic acid bacteria used in the food industry, *Streptococcus, Lactococcus, Lactobacillus, Leuconostoc, Pediococcus* and *Bifidobacterium* are predominantly applied. The lactic acid bacteria of the species *Streptococcus thermophilus* (*S. thermophilus*) are used extensively alone or in combination with other bacteria such as *Lactobacillus delbrueckii* subsp *bulgaricus* (*L. bulgaricus*) for the production of food products, in particular fermented food products. They are used in particular in the formulation of the ferments used for the production of fermented milks, for example yoghurt. Certain of them play a dominant role in the development of the texture of the fermented product. This characteristic is closely linked to the production of extracellular polymeric substances that are secreted by the lactic acid bacteria into the surrounding environment.

The current trend in yoghurt production is aiming for mild flavor and high texture. Today this is achieved by the use of cultures which produce a mild flavor and the addition of thickeners or proteins to give the desired thickness. Yoghurt producers would like to be able to make yoghurt with these properties without the addition of thickening agents. This will help them reduce cost and give a cleaner label. One very attractive way to achieve this would be to have a starter culture which produces a high level of texture.

Several strains of *S. thermophilus* and *L. bulgaricus* produce exopolysaccharides. These molecules may be associated with the cell wall, or they may be liberated into the medium as a loose, slime-like substance (i.e., "ropy" polysaccharide). Although the presence of exopolysaccharide does not confer any obvious advantage to growth or survival of *S. thermophilus* or *L. bulgaricus* in milk, in situ production by these species or other dairy lactic acid bacteria typically imparts a desirable "ropy" or viscous texture to fermented milk products. Work has also shown that exopolysaccharide-producing *S. thermophilus* can enhance the functional properties of Mozzarella cheese. For further details see the review article of Broadbent et al. (J. dairy Sci. 86:407-423).

In order to meet the requirements of the industry, it has become necessary to provide novel texturizing strains of lactic acid bacteria, in particular of *S. thermophilus*, for texturizing food products. Especially there is a need for novel texturizing strains of *S. thermophilus* which can be used together with texturizing strains of *Lactobacillus* such as e.g. *L. bulgaricus*.

SUMMARY OF THE INVENTION

The problem to be solved by the present invention is to provide novel *S. thermophilus* strains with improved properties in particular in relation to their ability to improve texture of fermented food products like dairy products such as e.g. yogurt as well as dairy analogue products and which is useful in present-day highly industrialized fermented food production.

Thus, an aspect of the present invention relates to a composition comprising:

(a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

In a further aspect the present invention relates to a method of producing a fermented product, comprising fermenting a substrate with:

(a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, or a composition according to the present invention.

In a further aspect the present invention relates to a fermented product obtainable by the method of the present invention.

In yet an aspect the present invention relates to a fermented product comprising:

(a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

In an aspect the invention relates to the use of:

(a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, for the manufacture of a fermented product.

In yet another aspect the present invention relates to a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1.

In a further aspect the present invention relates to a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

BRIEF DESCRIPTION OF THE SEVERAL VIEWS OF THE DRAWINGS

FIG. 1: Promoter region of galactokinase genes (galK). The position of the mutation in the galk promoter region of DSM 33118 is indicated with grey color code. The published galK gene sequence from *S. thermophilus* ST111 (Genbank accession no. AY704368) is indicated for comparison. −35: −35-promoter box; −10: −10-promoter box; RBS: ribosome binding site.

DETAILED DESCRIPTION OF THE INVENTION

Definitions

Figure 2:
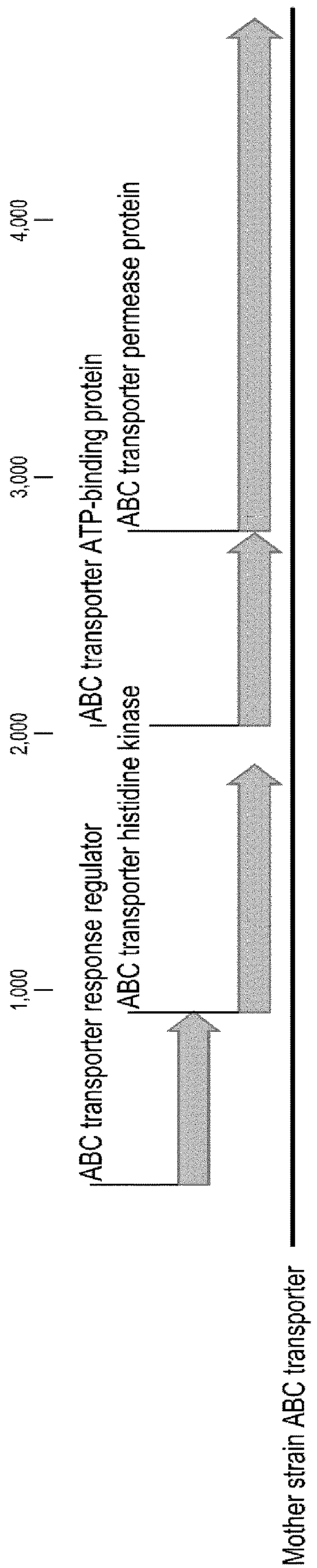
FIG. 2: Organisation of the ABC transporter operon of the mother strain of DSM 33118 showing the four genes "ABC transporter response regulator", "ABC transporter histidine kinase", ABC transporter ATP-binding protein", and ABC transporter permease protein" (short for "ABC transporter sensor and permease protein").

Prior to outlining the present invention in more details, a set of terms and conventions is first defined:

The term "milk" is to be understood as the lacteal secretion obtained by milking any mammal, such as cows, sheep, goats, buffaloes or camels. In a preferred embodiment, the milk is cow's milk. The term milk also includes protein/fat solutions made partly or exclusively of plant materials.

Dairy analogue products can be prepared using the presently disclosed strains of *S. thermophilus*. The term "dairy analogue" as used herein is meant to refers to dairy-like products, which are products used as culinary replacements for dairy products, prepared where one or more milk constituents have been replaced with other ingredients and the resulting food resembles the original product. The milk constituents are replaced completely or substantially with plant material, for example, using planted-based milks derived from legumes (such as soybeans), nuts (such as coconut), cereals (such as oat).

The term "legume" refers to any plant belonging to the family Fabaceae. Fabaceae is a large and economically important family of flowering plants, which is commonly known as the legume family, pea family, bean family or pulse family. A variety of different legumes can be consumed. Legumes typically have a pod or hull that opens along two sutures when the seeds of the legume are ripe.

The term "nuts" as used herein can be true nuts from tree or shrubs or culinary nuts which may be drupaceous nuts or seeds that are nut-like. In botanical terms, a nut is a dry one-seeded fruit which is indehiscent (i.e., it does not split open along a definite seam at maturity). Culinary nuts are those that are not botanically qualified as nuts, but that have a similar appearance and culinary role. Many culinary nuts are seeds of a drupe, referred herein as drupaceous nuts. A drupe is an indehiscent fruit in which an outer fleshy part surrounds a single shell (the pit or stone) hardened endocarp with a seed inside. Drupaceous nuts are seed of drupes.

The term "cereal" refers to both true cereal and pseudocereal. True cereal refers to the seeds of plants of the Poaceae family. Pseudocereal are seed of plants which do not belong to Poaceae family but are used in much the same way as cereals.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder or the milk substrate may originate from a plant material. Preferably, at least part of the protein in the milk substrate is (i) proteins naturally occurring in mammalian milk, such as casein or whey protein or (ii) proteins naturally occurring in plant milk. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a fermented product such as a dairy or dairy analogue product in solid or liquid form (fermented milk product).

In the present context the term "starter culture" is a culture which is a preparation (composition) of one or more bacterial strains (such as lactic acid bacteria strains) to assist the beginning of the fermentation process in preparation of fermented products such as various foods, feeds and beverages.

In the present context, a "yoghurt starter culture" is a bacterial culture which comprises one or more *Lactobacillus* selected from a *Lactobacillus delbrueckii* subsp *bulgaricus* (*L. bulgaricus*) strain and/or a *Lactobacillus acidophilus* strain and one or more *Streptococcus thermophilus* (*S. thermophilus*) strain. In accordance herewith, a "yoghurt" refers to a fermented milk product obtainable by inoculating and fermenting a milk substrate with a composition comprising a *Lactobacillus* strain such as *L. bulgaricus* and/or *L. acidophilus* and a *S. thermophilus* strain.

In the present context, the term "galactose-positive *S. thermophilus* strain" or "gal-positive *S. thermophilus* strain" or "gal+ *S. thermophilus* strain" as defined herein means that pH is reduced by a value of at least 1.0 after 16 hours incubation at 37° C. in M17 with 2% galactose (galactose added as sole carbohydrate), inoculated in an amount of at least $10^4$ cells pr ml. It has been observed that galactose positive derivatives often exhibited a slower acidification profile and had a higher end pH after more than 20 hours of fermentation.

In the present context, the term "mutant" or "mutant strain" should be understood as a strain derived, or a strain which can be derived, from a strain of the invention (or the mother strain) by means of e.g. genetic engineering, radiation and/or chemical treatment. It is preferred that the mutant is a functionally equivalent mutant, e.g. a mutant that has substantially the same, or improved, properties (e.g. regarding texture, shear stress, viscosity, gel firmness, mouth coating, flavour, post acidification, acidification speed, and/or phage robustness) as the strain from which it is derived. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less than 5%, or less than 1% or even less than 0.1% of the nucleotides in the bacterial genome have been shifted with another nucleotide, or deleted, compared to the mother strain. As will be clear to the skilled person mutants of the present invention can also be mother strains.

In the present context, the term "variant" or "variant strain" should be understood as a strain which is functionally equivalent to a strain of the invention, e.g. having substantially the same, or improved, properties e.g. regarding texture, shear stress, viscosity, gel firmness, mouth coating, flavour, post acidification, acidification speed, and/or phage robustness). Such variants, which may be identified using appropriate screening techniques, are a part of the present invention.

For purposes of the present invention, the degree of identity between two amino acid sequences is determined using the Needleman-Wunsch algorithm (Needleman and Wunsch (1970) J. Mol. Biol. 48: 443-453) as implemented in the Needle program of the EMBOSS package (EMBOSS: The European Molecular Biology Open Software Suite, Rice et al. (2000) Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labelled "longest identity" (obtained using the –no brief option) is used as the percent identity and is calculated as follows:

$$(\text{Identical Residues} \times 100)/(\text{Length of Alignment} - \text{Total Number of Gaps in Alignment})$$

In the present description and claims the conventional one-letter and three-letter codes for amino acid residues are used. For ease of reference, amino acid changes in mutants and variants of the invention are described by use of the following nomenclature: amino acid residue in the parent enzyme; position; substituted amino acid residue(s). According to this nomenclature, the substitution of, for instance, an alanine residue for a glycine residue at position 20 is indicated as Ala20Gly or A20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as DELTA(Ala20-Gly21) or DELTA(A20-G21). When a parent enzyme sequence contains a deletion in comparison to the enzyme sequence used for numbering an insertion in such a position (e.g. an alanine in the deleted position 20) is indicated as *20Ala or*20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y, V).

In the context of the present invention, a mutation in the gene (gene mutation) is to be understood as an alteration in the nucleotide sequence of the genome of an organism resulting in changes in the phenotype of said organism, wherein the alteration may be a deletion of a nucleotide, a substitution of a nucleotide by another nucleotide, an insertion of a nucleotide, or a frameshift. In the context of the present invention, a deletion is to be understood as a genetic mutation resulting in the removal of one or more nucleotides of a nucleotide sequence of the genome of an organism; a insertion is to be understood as the addition of one or more nucleotides to the nucleotide sequence; a substitution (or point mutation) is to be understood as a genetic mutation where a nucleotide of a nucleotide sequence is substituted by another nucleotide; a frameshift is to be understood as a genetic mutation caused by a insertion or deletion of a number of nucleotides in a nucleotide sequence that is not divisible by three, therefore changing the reading frame and resulting in a completely different translation from the original reading frame; an introduction of a stop codon is to be understood as a point mutation in the DNA sequence resulting in a premature stop codon; a inhibition of substrate binding of the encoded protein is to be understood as any mutation in the nucleotide sequence that leads to a change in the protein sequence responsible for preventing binding of a substrate to its catalytic site of the protein. Furthermore, a knockout mutant is to be understood as genetic mutation resulting in the removal or deletion of a gene, such as an entire gene or an entire open reading frame from the genome of an organism.

In the present description and claims the conventional one-letter code for nucleotides is used following the analogous principles as described for amino acids nomenclature supra.

Algorithms for aligning sequences and determining the degree of sequence identity between them are well known in the art. For the purpose of the present invention a process may be carried out for aligning nucleotide sequences using blastn as provided by the National Center for Biotechnology Information (NCBI) on https://blast.ncbi.nlm.nih.gov applying standard parameter.

The term "Tellurite resistant" is to be understood as a bacterial strain which is able to grow (form a colony) on M17-2% lactose agar plates containing 0.1 mM K2Te03 after 1 to 3 days of incubation at 37° C.

The term "Bacitracin resistant" is to be understood as a bacterial strain which is able to grow (form a colony) on M17-2% lactose agar plates containing at least 0.5 μg/ml bacitracin after 1 days of incubation at 37° C. anaerobically.

Viscosity is measured as disclosed in Example 2.

Shear stress is measured as disclosed in Example 5

Complex Modulus is measured as disclosed in Example 6

The inventors have surprisingly identified several *S. thermophilus* strains that fulfil the needs of the industry. The new strains show e.g. improved rheological properties (e.g. texture), when applied alone or as part of a mixed culture in a dairy substrate when compared to its mother strain. The novel *S. thermophilus* strains have the capacity to be used in e.g. dairy cultures such as yoghurt cultures to obtain improved rheological parameters, such as shear stress (i.e. viscosity) and gel firmness of the final product. In the present application the term gel stiffness and the term gel firmness will be used herein interchangeably. Rheology is closely linked to sensory quality of the product and the interplay between rheology and taste in the final product is therefore of outmost importance.

Composition

Thus, one aspect of the present invention relates to a composition comprising (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

Further specification of the *S. thermophilus* in a) and b) above can be found infra i.e. in the parts termed "Novel *Streptococcus thermophilus* strain having a mutation in the −10-promotor box of the galK gene and applications thereof" and "Novel *Streptococcus thermophilus* strains having a mutation in a gene in the ABC transporter operon and applications thereof".

The composition of the present invention may be provided in several forms. It may be a powder, pellets or tablets. It may be a frozen form, dried form, freeze dried form, or liquid form. Thus, in one embodiment the composition is in frozen, dried, freeze-dried or liquid form.

The composition of the present invention may additionally comprise cryoprotectants, lyoprotectants, antioxidants, nutrients, fillers, flavorants or mixtures thereof. The composition preferably comprises one or more of cryoprotectants, lyoprotectants, antioxidants and/or nutrients, more preferably cryoprotectants, lyoprotectants and/or antioxidants and most preferably cryoprotectants or lyoprotectants, or both. Use of protectants such as cryoprotectants and lyoprotectant are known to a skilled person in the art. Suitable cryoprotectants or lyoprotectants include mono-, di-, tri- and polysaccharides (such as glucose, mannose, xylose, lactose, sucrose, trehalose, raffinose, maltodextrin, starch and gum arabic (acacia) and the like), polyols (such as erythritol, glycerol, inositol, mannitol, sorbitol, threitol, xylitol and the like), amino acids (such as proline, glutamic acid), complex substances (such as skim milk, peptones, gelatin, yeast extract) and inorganic compounds (such as sodium tripolyphosphate).

In one embodiment, the composition according to the present invention may comprise one or more cryoprotective agent(s) selected from the group consisting of inosine-5'-monophosphate (IMP), adenosine −5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds. Suitable antioxidants include ascorbic acid, citric acid and salts thereof, gallates, cysteine, sorbitol, mannitol, maltose. Suitable nutrients include sugars, amino acids, fatty acids, minerals, trace elements, vitamins (such as vitamin B-family, vitamin C). The composition may optionally comprise further substances including fillers (such as lactose, maltodextrin) and/or flavorants.

In one embodiment of the invention the cryoprotective agent is an agent or mixture of agents, which in addition to its cryoprotectivity has a booster effect.

The expression "booster effect" is used to describe the situation wherein the cryoprotective agent confers an increased metabolic activity (booster effect) on to the thawed or reconstituted culture when it is inoculated into the medium to be fermented or converted. Viability and metabolic activity are not synonymous concepts. Commercial frozen or freeze-dried cultures may retain their viability, although they may have lost a significant portion of their metabolic activity e.g. cultures may lose their acid-producing (acidification) activity when kept stored even for shorter periods of time. Thus viability and booster effect has to be evaluated by different assays. Whereas viability is assessed by viability assays such as the determination of colony forming units, booster effect is assessed by quantifying the relevant metabolic activity of the thawed or reconstituted culture relative to the viability of the culture. The term "metabolic activity" refers to the oxygen removal activity of the cultures, its acid-producing activity, i. e. the production of e. g. lactic acid, acetic acid, formic acid and/or propionic acid, or its metabolite producing activity such as the production of aroma compounds such as acetaldehyde, (a-acetolactate, acetoin, diacetyl and 2,3-butylene glycol (butanediol)).

In one embodiment the composition of the invention contains or comprises from 0.2% to 20% of the cryoprotective agent or mixture of agents measured as % w/w of the material. It is, however, preferable to add the cryoprotective agent or mixture of agents at an amount which is in the range from 0.2% to 15%, from 0.2% to 10%, from 0.5% to 7%, and from 1% to 6% by weight, including within the range from 2% to 5% of the cryoprotective agent or mixture of agents measured as % w/w of the frozen material by weight. In a preferred embodiment the culture comprises approximately 3% of the cryoprotective agent or mixture of agents measured as % w/w of the material by weight. The amount of approximately 3% of the cryoprotective agent corresponds to concentrations in the 100 mM range. It should be recognized that for each aspect of embodiment of the invention the ranges may be increments of the described ranges.

In a further aspect, the composition of the present invention contains or comprises an ammonium salt (e.g. an ammonium salt of organic acid (such as ammonium formate and ammonium citrate) or an ammonium salt of an inorganic acid) as a booster (e.g. growth booster or acidification booster) for bacterial cells, such as cells belonging to the species *S. thermophilus*, e.g. (substantial) urease negative bacterial cells. The term "ammonium salt", "ammonium formate", etc., should be understood as a source of the salt or a combination of the ions. The term "source" of e.g. "ammonium formate" or "ammonium salt" refers to a compound or mix of compounds that when added to a culture of cells, provides ammonium formate or an ammonium salt. In some embodiments, the source of ammonium releases ammonium into a growth medium, while in other embodiments, the ammonium source is metabolized to produce ammonium. In some preferred embodiments, the ammonium source is exogenous. In some particularly preferred embodiments, ammonium is not provided by the dairy substrate. It should of course be understood that ammonia may be added instead of ammonium salt. Thus, the term ammonium salt comprises ammonia (NH3), NH4OH, NH4+, and the like.

In one embodiment the composition of the invention may comprise thickener and/or stabilizer, such as pectin (e.g. HM pectin, LM pectin), gelatin, CMC, Soya Bean Fiber/Soya Bean Polymer, starch, modified starch, carrageenan, alginate, and guar gum In one embodiment wherein the microorganism produces a polysaccharide (such as EPS) which causes a high/ropy texture in the acidified milk product the acidified milk product is produced substantially free, or completely free of any addition of thickener and/or stabilizer, such as pectin (e.g. HM pectin, LM pectin), gelatin, CMC, Soya Bean Fiber/Soya Bean Polymer, starch, modified starch, carrageenan, alginate, and guar gum. By substantially free should be understood that the product comprise from 0% to 20% (w/w) (e.g. from 0% to 10%, from 0% to 5% or from 0% to 2% or from 0% to 1%) thickener and/or stabilizer.

The composition may be a mixture or as a kit-of-parts comprising, i) the *Streptococcus thermophilus* according to (a) above and/or (ii) the *Streptococcus thermophilus* according to (b) above and iii) at least one strain belonging to the genus *Lactobacillus*. It may be contemplated that the at least one strain belonging to the genus *Lactobacillus* is selected from *Lactobacillus delbrueckii* subsp *bulgaricus, Lactobacillus acidophilus, Lactobacillus casei, Lactobacillus paracasei*, and/or *Lactobacillus rhamnosus*.

Thus, it may be contemplated that the composition may be a mixture or as a kit-of-parts comprising, (i) a *S. thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (ii) a *S. thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein and iii) at least one strain belonging to the genus *Lactobacillus*. It may be contemplated that the at least one strain belonging to the genus *Lactobacillus* is selected from *Lactobacillus delbrueckii* subsp *bulgaricus, Lactobacillus acidophilus, Lactobacillus casei, Lactobacillus paracasei*, and/or *Lactobacillus rhamnosus*.

In an embodiment the (i) *S. thermophilus* according to (a) above is *S. thermophilus* strain DSM 33118 or mutants or variants thereof and (ii) the *S. thermophilus* according to (b) above is a *S. thermophilus* strain selected from the group consisting of DSM 33745 or mutants or variants thereof, DSM 33746 or mutants or variants thereof, DSM 33747 or mutants or variants thereof and combinations thereof.

In a further embodiment the at least one strain belonging to species *L. bulgaricus* is strain DSM 33571 or mutants or variants thereof.

Thus, in a preferred embodiment the composition and/or mixture or kit-of-parts comprises *S. thermophilus* strains DSM 33118 and/or DSM 33745 and *L. bulgaricus* strain DSM 33571.

Thus, in a preferred embodiment the composition and/or mixture or kit-of-parts comprises *S. thermophilus* strains DSM 33118 and/or DSM 33746 and *L. bulgaricus* strain DSM 33571.

Thus, in a preferred embodiment the composition and/or mixture or kit-of-parts comprises *S. thermophilus* strains DSM 33118 and/or DSM 33747 and *L. bulgaricus* strain DSM 33571.

In order to obtain the best combination of acidity, taste, texture of a product such as a dairy product, like yoghurt, a combination of *S. thermophilus* and *L. bulgaricus* is often applied. Example 8 shows that a mixed culture comprising *S. thermophilus* and *L. bulgaricus* provided improvement in shear stress when compared to a proprietary mixed culture when applied in the production of yoghurt.

Probiotic Strains

The term "probiotic bacteria" refers to viable bacteria which are administered in adequate amounts to a consumer for the purpose of achieving a health-promoting effect in the consumer. Probiotic bacteria are capable of surviving the conditions of the gastrointestinal tract after ingestion and colonize the intestine of the consumer. Probiotic bacterial strains may be added before or after fermentation. If added before fermentation the probiotic bacterial strain also act as a fermentative bacteria.

It will be appreciated that the *Lactobacillus* genus taxonomy was updated in 2020. The new taxonomy is disclosed in Zheng et al. 2020 and will be cohered to herein if not otherwise indicated. For the purpose of the present invention, the table below presents a list of new and old names of some *Lactobacillus* species relevant to the present invention.

TABLE 1

New and old names of some *Lactobacillus* species relevant to the present invention.

| Old Name | New Name |
|---|---|
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |
| *Lactobacillus casei* | *Lacticaseibacillus casei* |
| *Lactobacillus paracasei* subsp. *paracasei* | *Lacticaseibacillus paracasei* subsp. *Paracasei* |
| *Lactobacillus plantarum* subsp. *plantarum* | *Lactiplantibacillus plantarum* subsp. *plantarum* |
| *Lactobacillus fermentum* | *Limosilactobacillus fermentum* |
| *Lactobacillus animalis* | *Ligilactobacillus animalis* |
| *Lactobacillus buchneri* | *Lentilactobacillus buchneri* |
| *Lactobacillus curvatus* | *Latilactobacillus curvatus* |
| *Lactobacillus futsaii* | *Companilactobacillus futsaii* |
| *Lactobacillus sakei* subsp. *sakei* | *Latilactobacillus sakei* subsp. |
| *Lactobacillus pentosus* | *Lactiplantibacillus pentosus* |

In a particular embodiment of the invention the probiotic strain according to the present invention is selected from the group consisting of bacteria of the genus *Lactobacillus*, such as *Lactobacillus acidophilus, Lacticaseibacillus paracasei, Lacticaseibacillus rhamnosus, Lacticaseibacillus casei, Lactobacillus delbrueckii, Lactobacillus lactis, Lactiplantibacillus plantarum, Limosilactobacillus reuteri* and *Lactobacillus johnsonii*, the genus *Bifidobacterium*, such as the *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*, and the like.

In a particular embodiment of the invention, the probiotic *Lactobacillus* strain is selected from the group consisting of *Lactobacillus acidophilus, Lacticaseibacillus paracasei, Lacticaseibacillus rhamnosus, Lactobacillus casei, Lactobacillus delbrueckii, Lactobacillus lactis, Lactiplantibacillus plantarum, Limosilactobacillus reuteri* and *Lactobacillus johnsonii.*

In a particular embodiment of the invention, the probiotic *Lactobacillus* strain is selected from the group consisting of a *Lacticaseibacillus rhamnosus* strain and a *Lacticaseibacillus paracasei* strain. In a particular embodiment of the invention, the probiotic strain is *Lacticaseibacillus rhamnosus* strain LGG® deposited as ATCC 53103.

In a particular embodiment of the invention, the probiotic strain is *Lacticaseibacillus paracasei* strain CRL 431 deposited as ATCC 55544.

In a particular embodiment of the invention, the probiotic strain is *Lactobacillus acidophilus* (LA-5®) deposited as DSM 13241.

In a particular embodiment of the invention, the probiotic *Bifidobacterium* strain is selected from the group consisting of *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis.*

In a particular embodiment of the invention, the probiotic *Bifidobacterium* probiotic strain is *Bifidobacterium animalis* subsp. *lactis* BB-12® deposited as DSM 15954.

The above mixtures or kit-of-parts may be further combined with other lactic acid bacteria such as but not limited to probiotic bacteria. In one embodiment the at least one lactic acid bacteria is selected from the group consisting of *Bifidobacterium* such as *Bifidobacterium animalis* subsp. *lactis* (e.g. BB-12®), *Lactobacillus acidophilus* (LA-5®), *Lacticaseibacillus rhamnosus* (e.g. LGG®) and any combinations thereof. Which *Bifidobacterium, Lactobacillus acidophilus* and/or *Lacticaseibacillus rhamnosus* to apply depend on their application and food to be produced.

In one embodiment the composition and/or mixture or kit-of-parts may comprise *S. thermophilus* strain DSM 33118 and/or DSM 33745, *L. bulgaricus* strain DSM 33571 and *Bifidobacterium animalis* subsp. *lactis* strain DSM 15954.

In one embodiment the composition and/or mixture or kit-of-parts may comprise *S. thermophilus* strain DSM 33118 and/or DSM 33746, *L. bulgaricus* strain DSM 33571 and *Bifidobacterium animalis* subsp. *lactis* strain DSM 15954.

In one embodiment the composition and/or mixture or kit-of-parts may comprise *S. thermophilus* strain DSM 33118 and/or DSM 33747, *L. bulgaricus* strain DSM 33571 and *Bifidobacterium animalis* subsp. *lactis* strain DSM 15954.

In one embodiment the mixture or kit-of-parts may comprise *S. thermophilus* strain DSM 33118 and/or DSM 33745, *L. bulgaricus* strain DSM 33571 and *Bifidobacterium animalis* subsp. *lactis* strain DSM15954 and *Lactobacillus acidophilus* strain DSM 13241.

In one embodiment the mixture or kit-of-parts may comprise *S. thermophilus* strain DSM 33118 and/or DSM 33746, *L. bulgaricus* strain DSM 33571 and *Bifidobacterium animalis* subsp. *lactis* strain DSM 15954 and *Lactobacillus acidophilus* strain DSM 13241.

In one embodiment the mixture or kit-of-parts may comprise *S. thermophilus* strain DSM 33118 and/or DSM 33747, *L. bulgaricus* strain DSM 33571 and *Bifidobacterium animalis* subsp. *lactis* strain DSM 15954 and *Lactobacillus acidophilus* strain DSM 13241.

In one embodiment the mixture or kit-of-parts may comprise *S. thermophilus* strain DSM 33118 and/or DSM 33745, *L. bulgaricus* strain DSM 33571 and *Lacticaseibacillus rhamnosus* strain ATCC 15954.

In one embodiment the mixture or kit-of-parts may comprise *S. thermophilus* strain DSM 33118 and/or DSM 33746, *L. bulgaricus* strain DSM 33571 and *Lacticaseibacillus rhamnosus* strain ATCC 53103.

In one embodiment the mixture or kit-of-parts may comprise *S. thermophilus* strain DSM 33118 and/or DSM 33747, *L. bulgaricus* strain DSM 33571 and *Lacticaseibacillus rhamnosus* strain ATCC 53103.

In one embodiment the mixture or kit-of-parts may comprise *S. thermophilus* strain DSM 33118 and/or DSM 33745, *L. bulgaricus* strain DSM 33571 and *Bifidobacterium animalis* subsp. *lactis* strain DSM 15954.

In one embodiment the mixture or kit-of-parts may comprise *S. thermophilus* strain DSM 33118 and/or DSM 33746, *L. bulgaricus* strain DSM 33571 and *Bifidobacterium animalis* subsp. *lactis* strain DSM 15954.

In one embodiment the mixture or kit-of-parts may comprise *S. thermophilus* strain DSM 33118 and/or DSM 33747, *L. bulgaricus* strain DSM 33571 and *Bifidobacterium animalis* subsp. *lactis* strain DSM 15954.

The expression "mixture" means that the strain(s) are physically mixed together. In an embodiment, the *S. thermophilus* strain(s) and the *Lactobacillus* strain(s) such as e.g. *Lactobacillus delbrueckii* subsp *bulgaricus, Lactobacillus acidophilus, Lactobacillus casei, Lactobacillus paracasei*, and/or *Lactobacillus rhamnosus* are in the same box or in the same pouch.

In contrast, the expression "A kit-of-part" comprising strain(s) means that strains or culture of strain(s) are physically separated but intended to be used together. Thus, the strains or culture of *S. thermophilus* strain(s) and *Lactobacillus* strain(s) are in different boxes or sachets. In an embodiment, the *S. thermophilus* strain(s) and the *Lactobacillus* such as e.g. *Lactobacillus delbrueckii* subsp *bulgaricus, Lactobacillus acidophilus, Lactobacillus casei, Lactobacillus paracasei*, and/or *Lactobacillus rhamnosus* strain(s) are under the same format, i.e., are in a frozen format, in the form of pellets or frozen pellets, a powder form, such as a dried or freeze-dried powder.

In a particular embodiment of the present invention, the composition comprises from $10^4$ to $10^{12}$ CFU (colony forming units)/g of the *S. thermophilus* strain, such as from 105 to $10^{11}$ CFU/g, from $10^6$ to $10^{10}$ CFU/g, or from $10^7$ to $10^9$ CFU/g of the *S. thermophilus* strain.

In a particular embodiment the composition further comprises from $10^4$ to $10^{12}$ CFU/g of the *Lactobacillus* strain, such as from 105 to $10^{11}$ CFU/g, such as from $10^6$ to $10^{10}$ CFU/g, or such as from $10^7$ to $10^9$ CFU/g of the *Lactobacillus* strain.

In a particular embodiment the composition comprises from $10^4$ to $10^{12}$ CFU/g, such as from 105 to $10^{11}$ CFU/g, from $10^6$ to $10^{10}$ CFU/g, or from $10^7$ to $10^9$ CFU/g of each of the *Lactobacillus delbrueckii* subsp *bulgaricus, Lactobacillus acidophilus, Lactobacillus casei, Lactobacillus paracasei*, and/or *Lactobacillus rhamnosus* strain(s).

*S. thermophilus* and *Lactobacillus* such as *L. bulgaricus, L. acidophilus, L. casei, L. paracasei*, and/or *L. rhamnosus* and other lactic acid bacteria are commonly used as starter cultures serving a technological purpose in the production of various foods, such as in the dairy industry, such as for fermented milk products. Thus, in another preferred embodiment the composition is suitable as a starter culture.

The composition may be a starter culture such as a yoghurt starter culture.

The composition and/or starter culture may be frozen, spray-dried, freeze-dried, vacuum-dried, air dried, tray dried or in liquid form. Typically, the storage stability of the composition and/or starter culture can be extended by formulating the product with low water activity. By controlling the water activity (Aw), it is possible to predict and regulate the effect of moisture migration on the product. Therefore, it may be preferred that the water activity (Aw) of the dried compositions herein is in the range from 0.01-0.8, preferably in the range from 0.05-0.4.

Method of Producing a Fermented Product

A further aspect of the present invention relates to a method of producing a fermented product, comprising fermenting a substrate with (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, or a composition of the present invention.

Depending on the product to be produced the substrate may be a milk substrate. A milk substrate is particularly preferred when fermented milk products such as yoghurt, buttermilk or kefir is the final product.

The milk substrate may be an animal or plant derived product. Thus, in an embodiment the fermented product is a food product such as a dairy product or a dairy analogue product. The dairy product may be selected from the group consisting of a fermented milk product such as but not limited to yoghurt, buttermilk and kefir or cheese such as but not limited to fresh cheese or pasta filata.

Even though the fermented product and/or the food product itself comprise acid and flavor generated during fermentation it may be desired that fermented product and/or the dairy product comprises an ingredient selected from the group consisting of a fruit concentrate, a syrup, a probiotic bacterial strain or culture, a coloring agent, a thickening agent, a flavoring agent, a preserving agent and mixtures thereof.

Likewise an enzyme may be added to the substrate e.g. the milk substrate before, during and/or after the fermenting, the enzyme being selected from the group consisting of an enzyme able to crosslink proteins, transglutaminase, an aspartic protease, lactase, chymosin, rennet and mixtures thereof.

In one embodiment the fermented product may be in the form of a stirred type product, a set type product or a drinkable product.

Clearly another aspect of the present invention relates to a fermented product obtainable by the method of the present invention. An aspect of the present invention is therefore also a fermented product comprising (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, for the manufacture of a fermented product. The fermented product may be a food product such as a dairy or dairy analogue product.

A further aspect of the present invention relates to the use of (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, for the manufacture of a fermented product. Again the fermented product may be a food product such as a dairy or dairy analogue product.

Another aspect relates to a fermented product comprising (a) a *S. thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *S. thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, for the manufacture of a fermented product. The fermented product may be a food product such as a dairy or dairy analogue product.

Novel *S. thermophilus* Strain Having a Mutation in the −10-Promotor Box of the galK Gene Thus in one aspect of the invention relates to a *Streptococcus thermophilus* strain having a mutation in the −10-promotor box of the galactokinase (galK) gene, wherein said mutation is a substitution of nucleotide G to nucleotide A in a position corresponding to position 33 in SEQ ID NO: 1.

In one embodiment, the *Streptococcus thermophilus* strain having a mutation in the −10-promotor box of the galK gene comprises a nucleotide sequence which is at least 50% identical to SEQ ID NO: 1. Preferably, the *Streptococcus thermophilus* strain having a mutation in the −10-promotor box of the galK gene comprises a nucleotide sequence which is at least 60%, such as at least 70%, at least 80%, at least 90%, at least 95%, at least 96%, at least 97%, at least 98% or at least 99% identical to SEQ ID NO: 1.

The inventors surprisingly found that the mutation in the −10 box of the galK promoter which is changed from 5'-TACGAT-3' to 5'-TACAAT-3' resulted in significantly increased viscosity and by this also improved texturizing properties in fermented milk (see e.g. Example 2 (single strain) and Example 5 and 8 (mixed culture)).

In a preferred embodiment the *Streptococcus thermophilus* strain is DSM 33118 or mutants or variants thereof.

To ensure the applicability in industry it may be contemplated that the mutants or variants show the same or similar shear stress and/or gel firmness characteristics as DSM 33118.

In one embodiment, mutants or variants of the present invention comprises a nucleotide sequence which is at least 50% identical to SEQ ID NO: 1. Preferably, the mutants or variants of the present invention comprises a nucleotide sequence which is at least 60%, such as at least 70%, at least 80%, at least 90%, at least 95%, at least 96%, at least 97%, at least 98% or at least 99% identical to SEQ ID NO: 1.

In the present context the term "similar shear stress" is to be understood as a range spanning from 10% below the shear stress characteristics of DSM 33118 to 10% above the shear stress characteristics of DSM 33118, the range may also be 9% below/above the shear stress characteristics of DSM 33118, 8% below/above of the shear stress characteristics of DSM 33118, 7% below/above of the shear stress characteristics of DSM 33118, 6% below/above of the shear stress characteristics of DSM 33118, 5% below/above of the shear stress characteristics of DSM 33118, 4% below/above of the shear stress characteristics of DSM 33118, 3% below/above of the shear stress characteristics of DSM 33118, 2% below/above of the shear stress characteristics of DSM 33118 or 1% below/above of the shear stress characteristics of DSM 33118.

In the present context the term "similar gel firmness" is to be understood as a range spanning from 10% below the gel firmness characteristics of DSM 33118 to 10% above the gel firmness characteristics of DSM 33118, the range may also be 9% below/above the gel firmness characteristics of DSM 33118, 8% below/above of the gel firmness characteristics of DSM 33118, 7% below/above of the gel firmness characteristics of DSM 33118, 6% below/above of the gel firmness characteristics of DSM 33118, 5% below/above of the gel firmness characteristics of DSM 33118, 4% below/above of the gel firmness characteristics of DSM 33118, 3% below/above of the gel firmness characteristics of DSM 33118, 2% below/above of the gel firmness characteristics of DSM 33118, or 1% below/above of the gel firmness characteristics of DSM 33118.

In the above "characteristics" is to be understood in the context of the definition part where it's stated how to appropriately measure shear stress or gel firmness.

Methods for determining the texture of fermented products such as dairy or dairy analogue products include measuring the shear stress (viscosity) or gel firmness (complex modulus) of the fermented product and are readily available and known in the art and exemplified herein.

In one embodiment of the present invention the *S. thermophilus* strain DSM 33118 generates an efflux time greater than 50 seconds, such as e.g. 51, 52, 53, 54, 55, 56, or 57 seconds when measured by a 25 ml volumetric pipette after 16 hours of growth in in skimmed milk (0.5% fat) at 37° C. when inoculated in an amount of at least $10^7$ cells per ml of milk (Example 2).

In a preferred embodiment the *S. thermophilus* strain DSM 33118 generates a viscosity that is at least 1% improved when compared to its mother strain, such as 2%, 3%, 4%, 5%, 6%, 7%, 8%, 9%, or 10% when compared to its mother strain when measured by a 25 ml volumetric pipette after 16 hours of growth in in skimmed milk (0.5% fat) at 37° C. when inoculated in an amount of at least $10^7$ cells per ml of milk.

A shear stress greater than 40 Pa, 41 Pa, 42 Pa, 43 Pa, 44 Pa, 45 Pa, 50 Pa, 60 Pa, 70 Pa, 80 Pa, 90 Pa, or 100 Pa at 300 $s^{-1}$ when measured on a fermented product made by addition of a composition of DSM 33118 and at least one further lactic acid bacteria strain (mixed culture) may be desired as this resembles a sensory viscosity/mouth thickness which is preferred by a sensory panel. Shear stress is measured as described in Example 5.

By "texture" or "mouthfeel" are meant the product's physical and chemical interaction in the mouth.

In one embodiment the *Streptococcus thermophilus* strain according to the present invention is galactose positive. The *S. thermophilus* strain may be derived from a gal-positive or gal-negative mother strain. In a preferred embodiment the mother strain is gal-negative.

It has been unexpectedly found that mutants from *S. thermophilus* strains resistant towards tellurite salts as $K2TeO3$ are showing increased rheological properties. Thus, in one embodiment the *Streptococcus thermophilus* strain of the present invention (e.g. DSM 33118) is resistant to tellurite and/or salts or derivatives thereof.

Novel *S. thermophilus* Strains Having a Mutation in a Gene in the ABC Transporter Operon Thus in one aspect of the invention relates to a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

In one embodiment, the *S. thermophilus* strain having a mutation in the ABC transporter sensor linked histidine kinase gene comprises a nucleotide sequence which is at least 50% identical to SEQ ID NO: 2. Preferably, the *S. thermophilus* strain having a mutation in the ABC transporter sensor linked histidine kinase gene comprises a nucleotide sequence which is at least 60%, such as at least 70%, at least 80%, at least 90%, at least 95%, at least 96%, at least 97%, at least 98% or at least 99% identical to SEQ ID NO: 2.

In one embodiment, the *S. thermophilus* strain having a the ABC transporter sensor linked response regulator comprises a nucleotide sequence which is at least 50% identical to SEQ ID NO: 3. Preferably, the *S. thermophilus* strain having a the ABC transporter sensor linked response regulator comprises a nucleotide sequence which is at least 60%, such as at least 70%, at least 80%, at least 90%, at least 95%, at least 96%, at least 97%, at least 98% or at least 99% identical to SEQ ID NO: 3.

In one embodiment, the *S. thermophilus* strain having a mutation in the ABC transporter sensor and permease protein comprises a nucleotide sequence which is at least 50% identical to SEQ ID NO: 4. Preferably, the *S. thermophilus* strain having a mutation in the ABC transporter sensor and permease protein comprises a nucleotide sequence which is at least 60%, such as at least 70%, at least 80%, at least 90%, at least 95%, at least 96%, at least 97%, at least 98% or at least 99% identical to SEQ ID NO: 4.

In one embodiment the mutation in the ABC transporter sensor linked histidine kinase gene is in a position corresponding to position 692 in SEQ ID NO 2, in a further embodiment the mutation in the ABC transporter sensor linked response regulator is in a position corresponding to corresponding to position 530 in SEQ ID NO 3 and in yet an embodiment the mutation in the ABC transporter sensor and permease protein is in a position corresponding to position 1726 in SEQ ID NO 4.

In one embodiment the mutation in the ABC transporter sensor linked histidine kinase gene is a substitution of nucleotide T to nucleotide C in a position corresponding to position 692 in SEQ ID NO 2, in a further embodiment the mutation in the ABC transporter sensor linked response regulator is a substitution of nucleotide T to nucleotide C in a position corresponding to corresponding to position 530 in SEQ ID NO 3 and in yet an embodiment the mutation in the ABC transporter sensor and permease protein is a substitution of nucleotide T to nucleotide C in a position corresponding to position 1726 in SEQ ID NO 4.

In one embodiment, the *S. thermophilus* strain having a mutation in the ABC transporter sensor linked histidine kinase gene express a protein which has an amino acid sequence which is at least 50% identical to SEQ ID NO: 5. Preferably, the *S. thermophilus* strain having a mutation in the ABC transporter sensor linked histidine kinase gene express a protein which has an amino acid sequence which is at least 60%, such as at least 70%, at least 80%, at least 90%, at least 95%, at least 96%, at least 97%, at least 98% or at least 99% identical to SEQ ID NO: 5.

In one embodiment, the *S. thermophilus* strain having an ABC transporter sensor linked response regulator express a protein which has an amino acid sequence which is at least 50% identical to SEQ ID NO: 6. Preferably, the *S. thermophilus* strain having an ABC transporter sensor linked response regulator express a protein which has an amino acid sequence which is at least 60%, such as at least 70%, at least 80%, at least 90%, at least 95%, at least 96%, at least 97%, at least 98% or at least 99% identical to SEQ ID NO: 6.

In one embodiment, the *S. thermophilus* strain having a mutation in the ABC transporter sensor and permease protein express a protein which has an amino acid sequence which is at least 50% identical to SEQ ID NO: 7. Preferably, the *S. thermophilus* strain having a mutation in the ABC transporter sensor and permease protein express a protein which has an amino acid sequence which is at least 60%, such as at least 70%, at least 80%, at least 90%, at least 95%, at least 96%, at least 97%, at least 98% or at least 99% identical to SEQ ID NO: 7.

In an embodiment:

the mutation in the ABC transporter sensor linked histidine kinase gene is in a position corresponding to position 231 in SEQ ID NO 5, the mutation in the ABC transporter sensor linked response regulator is in a position corresponding to position 177 in SEQ ID NO 6, the mutation in the ABC transporter sensor and permease protein is in a position corresponding to position 576 in the SEQ ID NO 7.

In a corresponding embodiment the mutation in the ABC transporter sensor linked histidine kinase gene is a substitution of amino acid Leu to amino acid Ser in a position corresponding to 231 in SEQ ID NO 5, the mutation in the ABC transporter sensor linked response regulator is a substitution of amino acid Met to amino acid Thr in a position corresponding to 177 in SEQ ID NO 6 and the mutation in the ABC transporter sensor and permease protein is a substitution of amino acid Phe to amino acid Leu in a position corresponding to 576 in the SEQ ID NO 7.

In a specific embodiment the *Streptococcus thermophilus* strain is selected from the group consisting of DSM 33745, DSM 33746 and DSM 33747 or mutants or variants thereof.

The inventors surprisingly found that strains comprising the mutations in the table below showed significantly increased viscosity and by this also improved texturizing properties in fermented milk (see e.g. Example 4 (single strains) and Example 6-7 (mixed culture)).

TABLE 2

Mutations in the *S. thermophilus* mutants

| Mutant | Mutated gene | Nucleotide substitution | Amino acid substitution |
|---|---|---|---|
| DSM 33745 | ABC transporter sensor linked histidine kinase | T692C | Leu231Ser (L231S) |
| DSM 33746 | ABC transporter sensor linked response regulator | T530C | Met177Thr (M177T) |
| DSM 33747 | ABC transporter sensor and permease protein | T1726C | Phe576Leu (F576L) |

In order to maintain industrial applicability it may be contemplated that mutants and variants of the *Streptococcus thermophilus* strain having a mutation in one of the genes of the ABC transporter operon show the same or similar shear stress and/or gel firmness characteristics as DSM 33745, DSM 33746 and/or DSM 33747.

In one embodiment, the mutants or variants of the *S. thermophilus* strain having a mutation in the ABC transporter sensor linked histidine kinase gene comprises a nucleotide sequence which is at least 50% identical to SEQ ID NO: 2. Preferably, the mutants or variants of the *S. thermophilus* strain having a mutation in the ABC transporter sensor linked histidine kinase gene comprises a nucleotide sequence which is at least 60%, such as at least 70%, at least 80%, at least 90%, at least 95%, at least 96%, at least 97%, at least 98% or at least 99% identical to SEQ ID NO: 2.

In one embodiment, mutants or variants of the *S. thermophilus* strain having a mutation in the ABC transporter sensor linked response regulator comprises a nucleotide sequence which is at least 50% identical to SEQ ID NO: 3. Preferably, the mutants or variants of the *S. thermophilus* strain having a ABC transporter sensor linked response regulator comprises a nucleotide sequence which is at least 60%, such as at least 70%, at least 80%, at least 90%, at least 95%, at least 96%, at least 97%, at least 98% or at least 99% identical to SEQ ID NO: 3.

In one embodiment, mutants or variants of the *S. thermophilus* strain having a mutation in the ABC transporter sensor and permease protein comprises a nucleotide sequence which is at least 50% identical to SEQ ID NO: 4. Preferably, the mutants or variants of the *S. thermophilus* strain having a mutation in the ABC transporter sensor and permease protein comprises a nucleotide sequence which is at least 60%, such as at least 70%, at least 80%, at least 90%, at least 95%, at least 96%, at least 97%, at least 98% or at least 99% identical to SEQ ID NO: 4.

In one embodiment, mutants or variants of the *S. thermophilus* strain having a mutation in the ABC transporter sensor linked histidine kinase gene express a protein which has an amino acid sequence which is at least 50% identical to SEQ ID NO: 5. Preferably, the mutants or variants of the *S. thermophilus* strain having a mutation in the ABC transporter sensor linked histidine kinase gene express a protein which has an amino acid sequence which is at least 60%, such as at least 70%, at least 80%, at least 90%, at least 95%, at least 96%, at least 97%, at least 98% or at least 99% identical to SEQ ID NO: 5.

In one embodiment, mutants or variants of the *S. thermophilus* strain having a the ABC transporter sensor linked response regulator express a protein which has an amino acid sequence which is at least 50% identical to SEQ ID NO: 6. Preferably, the mutants or variants of the *S. thermophilus* strain having an ABC transporter sensor linked response regulator express a protein which has an amino acid sequence which is at least 60%, such as at least 70%, at least 80%, at least 90%, at least 95%, at least 96%, at least 97%, at least 98% or at least 99% identical to SEQ ID NO: 6.

In one embodiment, mutants or variants of the *S. thermophilus* strain having a mutation in the ABC transporter sensor and permease protein express a protein which has an amino acid sequence which is at least 50% identical to SEQ ID NO: 7. Preferably, the mutants or variants of the *S. thermophilus* strain having a mutation in the ABC transporter sensor and permease protein express a protein which has an amino acid sequence which is at least 60%, such as at least 70%, at least 80%, at least 90%, at least 95%, at least 96%, at least 97%, at least 98% or at least 99% identical to SEQ ID NO: 7.

In the present context the term "similar shear stress" is to be understood as a range spanning from 10% below the shear stress characteristics of DSM 33745, DSM 33746 and/or DSM 33747 to 10% above the shear stress characteristics of DSM 33745, DSM 33746 and/or DSM 33747, the range may also be 9% below/above the shear stress characteristics of DSM 33745, DSM 33746 and/or DSM 33747, such as 8% below/above of the shear stress characteristics of DSM 33745, DSM 33746 and/or DSM 33747, e.g. 7% below/above of the shear stress characteristics of DSM 33745, DSM 33746 and/or DSM 33747, such as 6% below/above of the shear stress characteristics of DSM 33118, e.g. 5% below/above of the shear stress characteristics of DSM 33745, DSM 33746 and/or DSM 33747, such as 4% below/above of the shear stress characteristics of DSM 33745, DSM 33746 and/or DSM 33747, e.g. 3% below/above of the shear stress characteristics of DSM 33745, DSM 33746 and/or DSM 33747, such as 2% below/above of the shear stress characteristics of DSM 33745, DSM 33746 and/or DSM 33747 or 1% below/above of the shear stress characteristics of DSM 33745, DSM 33746 and/or DSM 33747.

In the present context the term "similar gel firmness" is to be understood as a range spanning from 10% below the gel firmness characteristics of DSM 33745, DSM 33746 and/or DSM 33747 to 10% above the gel firmness characteristics of DSM 33745, DSM 33746 and/or DSM 33747, the range may also be 9% below/above the gel firmness characteristics of DSM 33745, DSM 33746 and/or DSM 33747, such as 8% below/above of the gel firmness characteristics of DSM 33745, DSM 33746 and/or DSM 33747, e.g. 7% below/above of the gel firmness characteristics of DSM 33118, such as 6% below/above of the gel firmness characteristics of DSM 33745, DSM 33746 and/or DSM 33747, e.g. 5% below/above of the gel firmness characteristics of DSM 33745, DSM 33746 and/or DSM 33747, such as 4% below/above of the gel firmness characteristics of DSM 33745, DSM 33746 and/or DSM 33747, e.g. 3% below/above of the gel firmness characteristics of DSM 33745, DSM 33746 and/or DSM 33747, such as 2% below/above of the gel firmness characteristics of DSM 33745, DSM 33746 and/or DSM 33747 or 1% below/above of the gel firmness characteristics of DSM 33745, DSM 33746 and/or DSM 33747.

In the above "characteristics" is to be understood in the context of the definition part where it's stated how to appropriately measure shear stress or gel firmness.

Methods for determining the texture of fermented products such as dairy or dairy analogue products include measuring the shear stress (viscosity) or gel firmness (complex modulus) of the fermented product and are readily available and known in the art and exemplified herein.

In one embodiment of the present invention the *S. thermophilus* strain DSM 33745, DSM 33746 and/or DSM 33747 generates an efflux time greater than 85 seconds when measured by a 25 ml volumetric pipette after 16 hours of growth in in skimmed milk (0.5% fat) at 37° C. when inoculated in an amount of at least $10^7$ cells per ml of milk (Example 4).

In one embodiment of the present invention the *S. thermophilus* strain DSM 33745 generates a stress greater than 45 Pa, 50 Pa, 60 Pa, 70 Pa, 80 Pa, 90 Pa, or 100 Pa at 300 $s^{-1}$ when measured on a fermented product made by addition of a composition of DSM 33745 and at least one further lactic acid bacteria strain (mixed culture) may be desired as this resembles a sensory viscosity/mouth thickness which is preferred by a sensory panel. Shear stress is measured as described above. Shear stress is measured as described in Example 6.

In one embodiment of the present invention the *S. thermophilus* strain DSM 33746 or DSM 33747 generates a stress greater than 38 Pa, 39 Pa, 40 Pa, 50 Pa, 60 Pa, 70 Pa, 80 Pa, 90 Pa, or 100 Pa at 300 $s^{-1}$ when measured on a fermented product made by addition of a composition of DSM 33747 and at least one further lactic acid bacteria strain (mixed culture) may be desired as this resembles a sensory viscosity/mouth thickness which is preferred by a sensory panel. Shear stress is measured as described above. Shear stress is measured as described in Example 8.

In one embodiment of the present invention the *S. thermophilus* strain DSM 33745 generates a complex modulus greater than 80 Pa, 85 Pa, 90 Pa, 95 Pa, 100 Pa, 105 Pa, 110 Pa, 115 Pa, 120 Pa, 125 Pa, 130 Pa, 135 Pa, 140 Pa, 145 Pa, or greater than 150 Pa when measured by oscillation at 1.52 Hz on a fermented product made by addition of a composition of DSM 33745 and at least one further lactic acid bacteria strain (mixed culture) may be desired as this resembles a sensory viscosity/mouth thickness which is preferred by a sensory panel. Complex modulus is measured as described above. Shear stress is measured as described in Example 6. The complex modulus is measured by oscillation at 1.52 Hz on a fermented product after 16 hours of growth in in skimmed milk (0.5% fat) at 43° C. when inoculated in an amount of at least $10^7$ cells per ml of milk.

In one embodiment of the present invention the *S. thermophilus* strain DSM 33746 or DSM 33747 generates a complex modulus greater than 105 Pa, 110 Pa, 115 Pa, 120 Pa, 125 Pa, 130 Pa, 135 Pa, 140 Pa, 145 Pa, or greater than 150 Pa when measured by oscillation at 1.52 Hz on a fermented product made by addition of a composition of DSM 33746 or DSM 33747 and at least one further lactic acid bacteria strain (mixed culture) may be desired as this resembles a sensory viscosity/mouth thickness which is preferred by a sensory panel. Complex modulus is measured as described above. Shear stress is measured as described in Example 7. The complex modulus is measured by oscillation at 1.52 Hz on a fermented product after 16 hours of growth in in skimmed milk (0.5% fat) at 43° C. when inoculated in an amount of at least $10^7$ cells per ml of milk.

In a preferred embodiment the *S. thermophilus* strain DSM 33745, DSM 33746 and/or DSM 33747 generates a viscosity that is at least 1% improved when compared to its mother strain, such as 2%, 3%, 4%, 5%, 6%, 7%, 8%, 9%, or 10% when compared to its mother strain when measured by a 25 ml volumetric pipette after 16 hours of growth in in skimmed milk (0.5% fat) at 37° C. when inoculated in an amount of at least $10^7$ cells per ml of milk.

By "texture" or "mouthfeel" are meant the product's physical and chemical interaction in the mouth.

In a further embodiment the *Streptococcus thermophilus* strain having a mutation in one of the genes in the ABC transporter operon is bacitracin resistant.

It has been unexpectedly found that mutants from *S. thermophilus* strains resistant towards bacitracin are showing increased texturizing properties. Thus, in one embodiment the *S. thermophilus* strains DSM 33745, DSM 33746 and DSM 33747 are resistant to bacitracin or derivatives thereof.

Furthermore, faster acidification was also observed in samples prepared with plant bases.

In a further embodiment the present invention provides fermented products comprising the *S. thermophilus* strain is selected from the group consisting of DSM 33745, DSM 33746 and DSM 33747 or mutants or variants thereof. The fermented product may be fermented dairy products which are plant based (such as plant-based cheese, yogurt, spread, butter, ice cream and the like), or dairy analogue products. To prepare dairy analogue products, a plant-based material can be used as starting material. Such material is of plant origin and comprises substantially plant materials. Dairy analogue products (or simply "dairy analogues") refer to dairy-like products. Examples include analogues of cheese, yogurt, spread, butter, ice cream and the like.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Any listing or discussion of an apparently prior published document in this specification should not necessarily be taken as an acknowledgement that the document is part of the state of the art or is common general knowledge.

Preferences, options and embodiments for a given aspect, feature or parameter of the invention should, unless the context indicates otherwise, be regarded as having been disclosed in combination with any and all preferences, options and embodiments for all other aspects, features and parameters of the invention. Embodiments and features of the present invention are also outlined in the following items and also illustrated by the following non-limiting examples.

DEPOSITS AND EXPERT SOLUTIONS

The applicant requests that a sample of the deposited microorganisms stated in the table below may only be made available to an expert, until the date on which the patent is granted.

TABLE 3

Deposits made at a Depositary institution having acquired the status of international depositary authority under the Budapest Treaty on the International Recognition of the Deposit of Microorganisms for the Purposes of Patent Procedure: *Leibniz Institute DSMZ-German Collection of Microorganisms and Cell Cultures* Inhoffenstr. 7B, 38124 Braunschweig, Germany.

| Strain | Accession No. | Deposit date |
|---|---|---|
| *Streptococcus thermophilus* | DSM 33118 | 2019 May 8 |
| *Streptococcus thermophilus* | DSM 33745 | 2021 Jan. 5 |
| *Streptococcus thermophilus* | DSM 33746 | 2021 Jan. 5 |
| *Streptococcus thermophilus* | DSM 33747 | 2021 Jan. 5 |

EXAMPLES

Example 1: Isolation and Characterization of *S. thermophilus* Mutants with Texturizing Properties Isolation of DSM 33118

An EPS-positive mother strain which does not grow on galactose as sole carbohydrate was streaked on M17 agar plates with 2% galactose (M17-gal plates) and incubated overnight. 0.1 ml from the overnight culture were plated on M17-gal plates and several colonies could be isolated after two days of growth at 37° C. Several mutants were purified on M17-gal plates and retested in M17 broth containing 2% galactose as sole carbohydrate.

A mutant was considered gal-positive when the pH was reduced by a value of at least 1.0 after 16 hours incubation in M17 with 2% galactose (galactose added as sole carbohydrate). While the mother strain did not lower the pH in M17-gal broth significantly, the purified mutant strain DSM 33118 reached a pH of 5.2 after 16 hours at 37° C., and was therefore considered a galactose positive mutant.

Sequencing of the Galactokinase Gene (galK) Promoter Region from DSM 33118

Sequencing of the beginning of the galK gene revealed a mutation in the region of the galk promoter of DSM 33118 (see FIG. 1). The mutation occurred at position 33 of the −10-promoter box of the galK gene where G was substituted by A in the nucleotide sequence. The mutation conferred DSM 33118 with a stronger promoter activity as compared with the mother strain, explaining the observed gal-positive phenotype. The consensus sequence for the −10-promoter box of the mother strain was "TACGAT", and substitution of nucleotide 4 ("G") of the −10 box for A leads to a −10 box with the sequence "TACAAT" present in DSM 33118.

It can be concluded that a mutation in the −10 box of the galK promoter (change from 5'-TACGAT-3' to 5'-TACAAT-3') resulted in significantly increased viscosity and by this to improved texturizing properties in fermented milk (see Example 2).

Example 2: Viscosity Test with the Galactose Positive Mutant DSM 33118

Coagulated milk was made from 200 ml semi-fat milk (1.5% fat) inoculated with 1% bacterial strains (from an overnight culture grown in M17 with 2% lactose at 37° C.), and incubated for 16 h at 37° C.

The viscosity of the coagulated milk was measured with a 25 ml volumetric pipette where the efflux time of said coagulated milk from the pipette was measured in triplicates. The coagulated milk is stirred carefully with a spoon to homogenize. The 25 ml volumetric pipette is then filled and the time to empty the pipette by gravity force is measured. The time it takes to empty 25 ml of coagulated milk from the pipette is noted as seconds.

TABLE 4

Pipette viscosity test results for *S. thermophilus* DSM 33118.

| | Efflux time Sample 1 | Efflux time Sample 2 | Efflux time Sample 3 | Average Efflux time (seconds) | Standard Deviation |
|---|---|---|---|---|---|
| Mother strain | 49 | 47 | 44 | 47 | 2.52 |
| DSM 33118 | 57 | 58 | 53 | 56 | 2.65 |

The average efflux time of 47 seconds for the mother strain and the average efflux time of 56 seconds for DSM 33118 indicates that the viscosity was increased by the mutant by 19% in the coagulated milk.

Example 3: Isolation and Characterization of the Texturizing Mutants DSM 33745, DSM 33746, and DSM 33747

A mother strain was inoculated from a M17-2% lactose overnight culture in M17-2% lactose with bacitracin concentrations of 0.3, 0.6, 0.9, and 1.2 μg/ml respectively and incubated overnight at 37° C. In all tubes except the one with 1.2 μg/ml bacitracin an OD600 above 2.50 was reached.

Based on this a M17-2% lactose overnight culture was plated on M17-2% lactose plates with bacitracin concentrations of 0.5 μg/ml and 1 μg/ml, respectively (0.1 ml per plate on 5 parallel plates), and incubated overnight at 37° C. anaerobically.

From the plates with the best appearance of single colonies, the ones containing 0.5 μg/ml bacitracin, 20 colonies were purified and further characterised. A number of purified clones showed increased viscosity measured by efflux test through a volumetric pipette (see example 2). The mutants with the best improved viscosity values were designated as DSM 33745, DSM 33746, and DSM 33747.

Genomic Analysis of Bacitracin Resistant Mutants:

The three bacitracin resistant mutants DSM 33745, DSM 33746, and DSM 33747 with improved texturing properties were fully genome sequenced and a genome comparison was performed to reveal mutations related to the improved phenotype. All three mutants DSM 33745, DSM 33746, and DSM 33747 showed mutations within an operon coding for an ABC transporter system. The organisation of the ABC transporter operon of the mother strain is shown in FIG. 2

TABLE 5

Mutations within ABC transporter region identified in the mutants DSM 33745, DSM 33746, and DSM 33747 as compared to the mother strain.

| Mutant | Mutated gene | Nucleotide mutation | Amino acid substitution |
|---|---|---|---|
| DSM 33745 | ABC transporter sensor linked histidine kinase | T692C | Leu231Ser (L231S) |
| DSM 33746 | ABC transporter sensor linked response regulator | T530C | Met177Thr (M177T) |
| DSM 33747 | ABC transporter sensor and permease protein | T1726C | Phe576Leu (F576L) |

For the three mutants DSM 33745, DSM 33746, and DSM 33747 the mutations occurred at different gene positions showing that these mutations were in fact independent and all leading to increased rheological properties.

Example 4: Viscosity Test with the Bacitracin Resistant Mutants DSM 33745, DSM 33746, and DSM 33747

Milk was inoculated 1% with bacterial strains (from an overnight culture grown in M17 with 2% lactose at 37° C.), and incubated for 16 h at 37° C.

The viscosity of the coagulated milk was measured in triplicates as described in Example 2.

TABLE 6

Pipette viscosity test results for the mother strain and the bacitracin resistant mutants of the mother strain DSM 33745, DSM 33746 and DSM 33747. The average efflux time of three measurements is shown.

| Sample | Efflux time (seconds) |
|---|---|
| Mother strain | 82 |
| DSM 33745 | 92 |
| DSM 33746 | 94 |
| DSM 33747 | 88 |

The efflux time of 82 seconds for the mother strain and the efflux time of 92, 94, and 88 seconds for DSM 33745, DSM 33746, and DSM 33747 respectively indicates that the viscosity was increased for the mutants by 12%, 15%, and 7% respectively in the coagulated milk.

Example 5: Application of DSM 33118 in the Production of Yoghurt

Materials and Methods

Milk base: 2.6% protein, 2.8% fat and 7% sucrose. Fresh milk and 38% cream with Arla Medium Heat Skimmed milk powder (SMP).

| | |
|---|---|
| Fermentation scale | 200 mL |
| Mixing of powder and re-hydration of milk base | Disperse powder in cold milk (<10° C.), heat to 58° C. (±2° C.) and rehydrate for 1 hour at 58° C. (±2° C.) with stirring |
| Homogenization | 200/50 bar at 65° C. |
| Pasteurization | 95° C. for 5 min |
| Culture inoculation | 500 U/2500 L (min. 1E10 cfu/g), inoculation at 43° C. |
| Fermentation temperature | 43° C. |
| Cut pH | pH 4.35 |
| Post treatment | Apply 2 bar before heat exchanger with outlet temperature set to 25° C. |

The samples shown in the following section is chosen from acidification speed, as it is well known, that acidification speed and shear stress is correlated. Only yoghurts with acidification speed of <450 minutes to pH 4.35 were chosen as data, to have comparable acidification speed with Premium 1.0.

Shear Stress—Correlating to Mouth Thickness

Shear stress was measured by using ASC rheometer model DSR502 from Anton Paar. The method is using a rotational step which is based on a rotational deformation on the sample, from 10-3 s−1 to 300 s−1, and then back to 10-3 s−1. The corresponding shear stress was measured. For these results, four shear rates (0.3; 30; 135; 300 s−1) were extracted from the flow curve (see Table). Samples were placed at 13° C. for 1 hour prior to measuring. Each sample was gently stirred with a spoon 5 times from bottom to top to assure a homogenous sample. The rheology cups were filled until the line and placed in the sample magazine. Samples were measured in duplicates using two separate yogurt cups. Measurements were conducted at day +7 and temperature of measurement is set to 13° C. Samples are stored at 5° C. until the day of measurement.

TABLE 7

Shear stress results measured by Anton Paar rheometer. The results are shown as average results, including the standard deviation from 2 replicate yoghurts for Premium 1.0 and for 12 different yoghurts containing the 28381. Measurements were conducted at day +7 adjusting the temperature to 13° C.

| Culture | 0.3 s−1 | 30 s−1 | 135 s−1 | 300 s−1 |
|---|---|---|---|---|
| Mixed cultures containing DSM 33118 | 2.53 ± 0.20 | 17.82 ± 1.38 | 37.66 ± 2.57 | 45.50 ± 0.19 |
| Premium 1.0 | 2.81 ± 0.11 | 17.2 ± 0.14 | 31.50 ± 0.00 | 40.10 ± 0.141 |

TABLE 8

Shear stress results measured by Anton Paar rheometer. Cultures other than Premium 1.0 are with DSM 33118 as the main strain. The results are shown as average results, including the standard deviation from 2 replicate yoghurts. Measurements were conducted at day +7 adjusting the temperature to 13° C.

| Culture | 0.3 s−1 | 30 s−1 | 135 s−1 | 300 s−1 |
|---|---|---|---|---|
| Culture 1 | 2.69 ± 0.04 | 17.10 ± 0.42 | 33.45 ± 0.92 | 42.30 ± 1.13 |
| Culture 2 | 2.37 ± 0.02 | 17.15 ± 0.35 | 37.20 ± 0.71 | 45.20 ± 0.28 |
| Culture 3 | 2.36 ± 0.16 | 17.90 ± 0.57 | 39.55 ± 0.78 | 47.10 ± 0.57 |
| Culture 4 | 2.42 ± 0.10 | 16.20 ± 0.57 | 36.50 ± 1.13 | 45.70 ± 0.99 |
| Culture 5 | 2.74 ± 0.34 | 19.90 ± 1.56 | 40.75 ± 1.77 | 47.45 ± 1.49 |
| Culture 6 | 2.61 ± 0.07 | 18.65 ± 0.50 | 38.50 ± 0.57 | 45.25 ± 0.21 |
| Premium 1.0 | 2.81 ± 0.11 | 17.20 ± 0.14 | 31.50 ± 0.00 | 40.10 ± 0.141 |

The different compositions i.e. starter cultures comprising DSM 33118 showed significantly higher shear stress, when compared to Premium 1.0. and thus improved texturizing property. Said improved texturizing property was apparent even when the other strains in the composition together with DSM 33118 was different. Therefor it is concluded that the improved texture is caused by the strain DSM 33118.

Example 6: Application of DSM 33745 in the Production of Yoghurt

Materials and Methods

Milk base: 2.6% protein, 2.8% fat and 7% sucrose. Fresh milk and 38% cream with Aria Medium Heat Skimmed milk powder (SMP).

| | |
|---|---|
| Fermentation scale | 200 mL |
| Mixing of powder and re-hydration of milk base | Disperse powder in cold milk (<10° C.), heat to 58° C. (±2° C.) and re-hydrate for 1 hour at 58° C. (±2° C.) with stirring |
| Homogenization | 200/50 bar at 65° C. |
| Pasteurization | 95° C. for 5 min |
| Culture inoculation | 500 U/2500 L (min. 1E10 cfu/g), inoculation at 43° C. |
| Fermentation temperature | 43° C. |
| Cut pH | pH 4.35 |
| Post treatment | Apply 2 bar before heat exchanger with outlet temperature set to 25° C. |

The strains were evaluated in a mixed culture with a set background of DSM 33118 and DSM33571 to simulate a yoghurt culture.

Complex Modulus G*—Correlating to Gel Firmness

Complex Modulus G* was evaluated by oscillation measurement using ASC rheometer model DSR502 from Anton Paar. The method is based on an oscillation step, where the sample is oscillated between two surfaces, with the upper geometry (bob) moving and the lower cup remaining stationary. The oscillation is performed from 0.5-8 Hz at constant strain. For these evaluations the results are extracted from measurements at 1.52 Hz. Samples are placed at 13° C. for 1 hour prior to measuring. Each sample is gently stirred with a spoon 5 times from bottom to top to assure a homogenous sample. The rheology cups are filled until the line and placed in the sample magazine. Samples are measured in duplicates using two separate yogurt cups. Measurements are conducted at day +7 and temperature of measurement is set to 13° C. Samples are stored at 5° C. until the day of measurement.

TABLE 9

| Gel firmness results measured by Complex Modulus G* by Oscillation at 1.52 Hz. The results are shown as average results, including the standard deviation from 2 replicate yoghurts. Measurements were conducted at day +7 adjusting the temperature to 13° C. | |
|---|---|
| Culture | Average results Complex Modulus G* at 1.52 Hz (Pa) n = 2 |
| Mother strain | 79.00 ± 1.70 |
| DSM 33745 | 95.35 ± 12.23 |

Shear Stress—Correlating to Mouth Thickness

Shear stress was measured by using ASC rheometer model DSR502 from Anton Paar. The method is using a rotational step which is based on a rotational deformation on the sample, from 10-3 s−1 to 300 s−1, and then back to 10-3 s−1. The corresponding shear stress is measured. For these results, four shear rates (0.3; 30; 135; 300 s−1) were extracted from the flow curve (see Table). Samples were placed at 13° C. for 1 hour prior to measuring. Each sample was gently stirred with a spoon 5 times from bottom to top to assure a homogenous sample. The rheology cups were filled until the line and placed in the sample magazine. Samples were measured in duplicates using two separate yogurt cups. Measurements were conducted at day +7 and temperature of measurement is set to 13° C. Samples were stored at 5° C. until the day of measurement.

TABLE 10

Shear stress results measured by Anton Paar rheometer. The results are shown as average results, including the standard deviation from 2 replicate yoghurts. Measurements were conducted at day +7 adjusting the temperature to 13° C.

| Culture | 0.3 s−1 | 30 s−1 | 135 s−1 | 300 s−1 |
|---|---|---|---|---|
| Mother strain | 2.37 ± 0.02 | 17.15 ± 0.35 | 37.20 ± 0.71 | 45.20 ± 0.64 |
| DSM 33745 | 2.74 ± 0.34 | 19.90 ± 1.56 | 40.75 ± 1.77 | 47.45 ± 1.49 |

When compositions comprising DSM 33745 was compared with compositions comprising the mother strain, both the gel firmness and the shear stress are increased. This shows the improvement conferred by DSM 33745, when compared directly to the mother strain.

Example 7: Application of DSM 33747 in the Production of Yoghurt

Materials and Methods

Milk base: 2.6% protein, 2.8% fat and 7% sucrose. Fresh milk and 38% cream with Aria Medium Heat Skimmed milk powder (SMP).

| | |
|---|---|
| Fermentation scale | 200 mL |
| Mixing of powder and re-hydration of milk base | Disperse powder in cold milk (<10° C.), heat to 58° C. (±2° C.) and re-hydrate for 1 hour at 58° C. (±2° C.) with stirring |
| Homogenization | 200/50 bar at 65° C. |
| Pasteurization | 95° C. for 5 min |
| Culture inoculation | 500 U/2500 L (min. 1E10 cfu/g), inoculation at 43° C. |
| Fermentation temperature | 43° C. |
| Cut pH | pH 4.35 |
| Post treatment | Apply 2 bar before heat exchanger with outlet temperature set to 25° C. |

The strains were evaluated in a mixed culture with a set background of DSM33540 and DSM24090 ST to simulate a yoghurt culture.

Complex Modulus G*—Correlating to Gel Firmness

Complex Modulus G*was evaluated by oscillation measurement using ASC rheometer model DSR502 from Anton Paar. The method wis based on an oscillation step, where the sample is oscillated between two surfaces, with the upper geometry (bob) moving and the lower cup remaining stationary. The oscillation is performed from 0.5-8 Hz at constant strain. For these evaluations the results are extracted from measurements at 1.52 Hz. Samples were placed at 13° C. for 1 hour prior to measuring. Each sample was gently stirred with a spoon 5 times from bottom to top to assure a homogenous sample. The rheology cups were filled until the line and placed in the sample magazine. Samples were measured in duplicates using two separate yogurt cups. Measurements were conducted at day +7 and temperature of measurement was set to 13° C. Samples were stored at 5° C. until the day of measurement.

TABLE 11

Gel firmness measured at 13° C. on day +7 by Complex Modulus G* by Oscillation at 1.52 Hz shown as average results and standard deviation from 2 individual yogurt cups.

| Culture | Average results Complex Modulus G* at 1.52 Hz (Pa) n = 2 |
|---|---|
| Mother strain | 101.90 ± 2.97 |
| DSM 33747 | 114.50 ± 6.36 |

Shear Stress—Correlating to Mouth Thickness

Shear stress was measured by using ASC rheometer model DSR502 from Anton Paar. The method is using a rotational step which is based on a rotational deformation on the sample, from 10-3 s−1 to 300 s−1, and then back to 10-3 s−1. The corresponding shear stress is measured. For these results, four shear rates (0.3; 30; 135; 300 s−1) were extracted from the flow curve (see Table). Samples were placed at 13° C. for 1 hour prior to measuring. Each sample was gently stirred with a spoon 5 times from bottom to top to assure a homogenous sample. The rheology cups were filled until the line and placed in the sample magazine. Samples were measured in duplicates using two separate yogurt cups. Measurements were conducted at day +7 and temperature of measurement was set to 13° C. Samples were stored at 5° C. until the day of measurement.

TABLE 12

Shear stress measured at 13° C. on day +7 by Anton Paar rheometer shown as average results and standard deviation from 2 individual yogurt cups.

| Culture | 0.3 s−1 | 30 s−1 | 135 s−1 | 300 s−1 |
|---|---|---|---|---|
| Mother strain | 3.10 ± 0.18 | 19.05 ± 0.50 | 32.20 ± 0.00 | 37.25 ± 0.21 |
| DSM 33747 | 3.44 ± 0.13 | 20.95 ± 0.78 | 34.95 ± 0.64 | 39.65 ± 0.21 |

When the strain DSM 33747 was combined with the same strains as the mother strain, both the gel firmness and the shear stress were increased. This shows the improvement of the DSM 33747, when compared directly to the mother strain.

Example 8: Application of DSM 33118 and DSM 33745 in the Production of Yoghurt

Materials and Methods

Milk base: 2.6% protein, 2.8% fat, 7% sucrose, 0.5% mod. starch. Ingredients: Fresh milk 3.5% fat (Arla), cream 9% fat (Arla), water, Thermtex modified starch (Ingredion) and Granulated sugar 550 (Nordic sugar).

Culture 1: (*L. bulgaricus* strain DSM 33571, *S. thermophilus* stains DSM 33118 and DSM 33745), F-DVS YoFlex® Premium 1.0: a proprietary prior art culture comprising one *L. bulgaricus* strain in combination with two different *S. thermophilus* strains.

| | |
|---|---|
| Fermentation scale | 3 L |
| Mixing of powder and re-hydration of milk base | Disperse powder in cold milk (<10° C.), heat to 58° C. (±2° C.) and re-hydrate for 1 hour at 58° C. (±2° C.) with stirring |
| Homogenization | 200/50 bar at 65° C. |
| Pasteurization | 95° C. for 5 min |
| Culture inoculation | 500 U/2500 L (min. 1E10 cfu/g), inoculation at 43° C. |
| Fermentation temperature | 43° C. |
| Cut pH | pH 4.35 |
| Post treatment | Apply 2 bar before heat exchanger with outlet temperature set to 20° C. |

Shear Stress—Correlating to Mouth Thickness

Shear stress was measured by using ASC rheometer model DSR502 from Anton Paar. The method is using a rotational step which is based on a rotational deformation on the sample, from 10-3 s−1 to 300 s−1, and then back to 10-3 s−1. The corresponding shear stress was measured. For these results, four shear rates (0.3; 30; 135; 300 s−1) were extracted from the flow curve (see Table). Samples were placed at 13° C. for 1 hour prior to measuring. Each sample was gently stirred with a spoon 5 times from bottom to top to assure a homogenous sample. The rheology cups were filled until the line and placed in the sample magazine. Samples were measured in duplicates using two separate yogurt cups. Measurements were conducted at day +7 and temperature of measurement is set to 13° C. Samples were stored at 5° C. until the day of measurement.

TABLE 13

Shear stress measured at 13° C. on day +7 by Anton Paar rheometer shown as average results and standard deviation from 2 individual yogurt cups.

| Culture | 0.3 s−1 | 30 s−1 | 135 s−1 | 300 s−1 |
|---|---|---|---|---|
| F-DVS YoFlex ® Premium 1.0 | 4.93 ± 0.08 | 24.30 ± 0.57 | 42.60 ± 0.28 | 48.85 ± 0.49 |
| Culture 1 | 5.11 ± 0.16 | 29.95 ± 1.06 | 54.65 ± 0.78 | 55.55 ± 0.21 |

Example 9: Application of DSM 33745 and DSM 24011 in the Preparation of Plant-Based Products Materials and Methods The following three plant milk bases were provided:

Oat base, 60% solution with tap water (obtained from 30% (wt) oat bran aqueous extraction and submitted to enzymatic treatment of partial hydrolysis and saccharification of starch, followed by heat treatment (Oatvita, Frulact, Portugal)). The 60% solution of oat base contains 1.3% fat and approximately 2.7% protein and 7.2% carbohydrates of which 5.4% glucose.

Coconut base (consisting of 51% of coconut milk (Aroy-D), 30% of natural coconut water (myCoco), 10% water, 3.5% starch (Clearam CH2020, Roquette) and 1% sucrose and 1% glucose (Nordic sugar))

Soy base (organic unsweetened soy milk (NATURLI' Foods A/S, Denmark) with addition of 3% sucrose (Nordic sugar))

All plant bases were pasteurized (90° C. for 20 minutes) after adding the sugars to avoid contamination. The bases were then cooled to 5° C.

Preparation of Samples and Fermentation

*S. thermophilus* DSM 24011 was chosen for comparison. It was disclosed in WO2012/052557 as high texturizing lactic acid bacteria for fermenting a milk substrate which may be soy milk. Frozen pelletized strains (F-DVS) of DSM 33745 and DSM 24011 were used to make a 1% solution in pepsal water, further diluted to inoculate approximately 1.00 E+06 CFU/mL in the soy, oat and coconut plant bases. Acidification tests were conducted using iCinac instrument (AMS alliance). Fermentations were carried out at 37° C., in 200 mL scale, removing the samples from incubation when pH reached 4.55 or for a max incubation time of 13 h.

Texture Analysis

The coagulum formed during fermentation was broken with a perforated disk and samples were run through the Micro Application Platform (MAP, 2 bars back-pressure; FH Scandinox A/S, Tarm, Denmark) at room temperature to allow the smoothing process. Samples were collected in 50 mL sterile cups and stored at 4° C. for 7 days. Then, a flow test and an oscillation test were performed with a rheometer DSR 301 (Anton Paar GmbH, Graz, Austria) set to 13° C. A stainless-steel coaxial cylinder (CC27 system) was used. The flow test was performed with shear rates ($\gamma$) from $10^{-3}$ 1/s to 300 1/s for the up-flow and from 300 1/s to $10^{-3}$ 1/s for the down-flow. Shear stress ($\tau$) was measured for each of the samples.

Results

Figure 3:
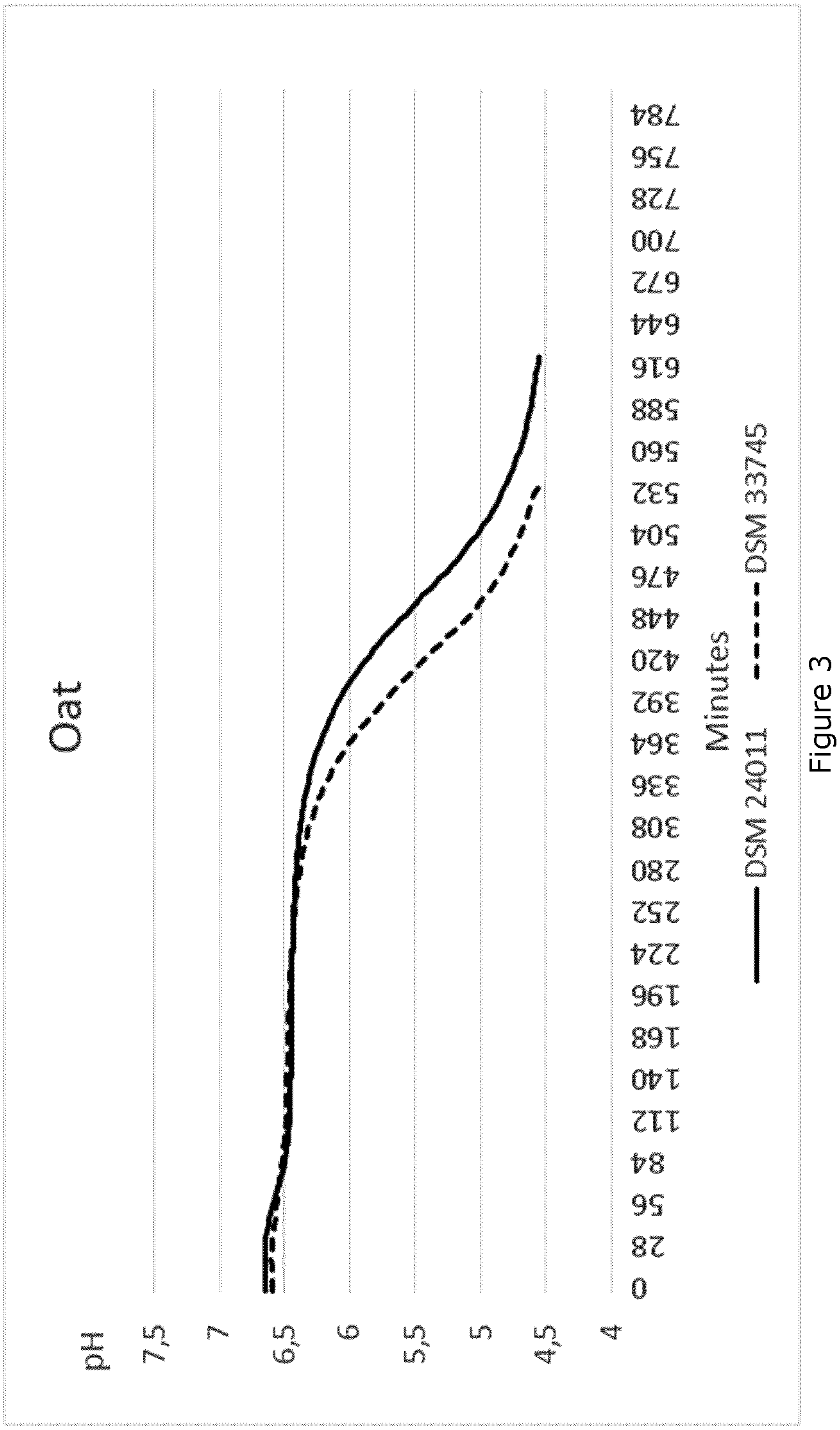
FIG. 3: Acidification profile of oat base fermented with DSM 33745 and DSM 24011
Figure 4:
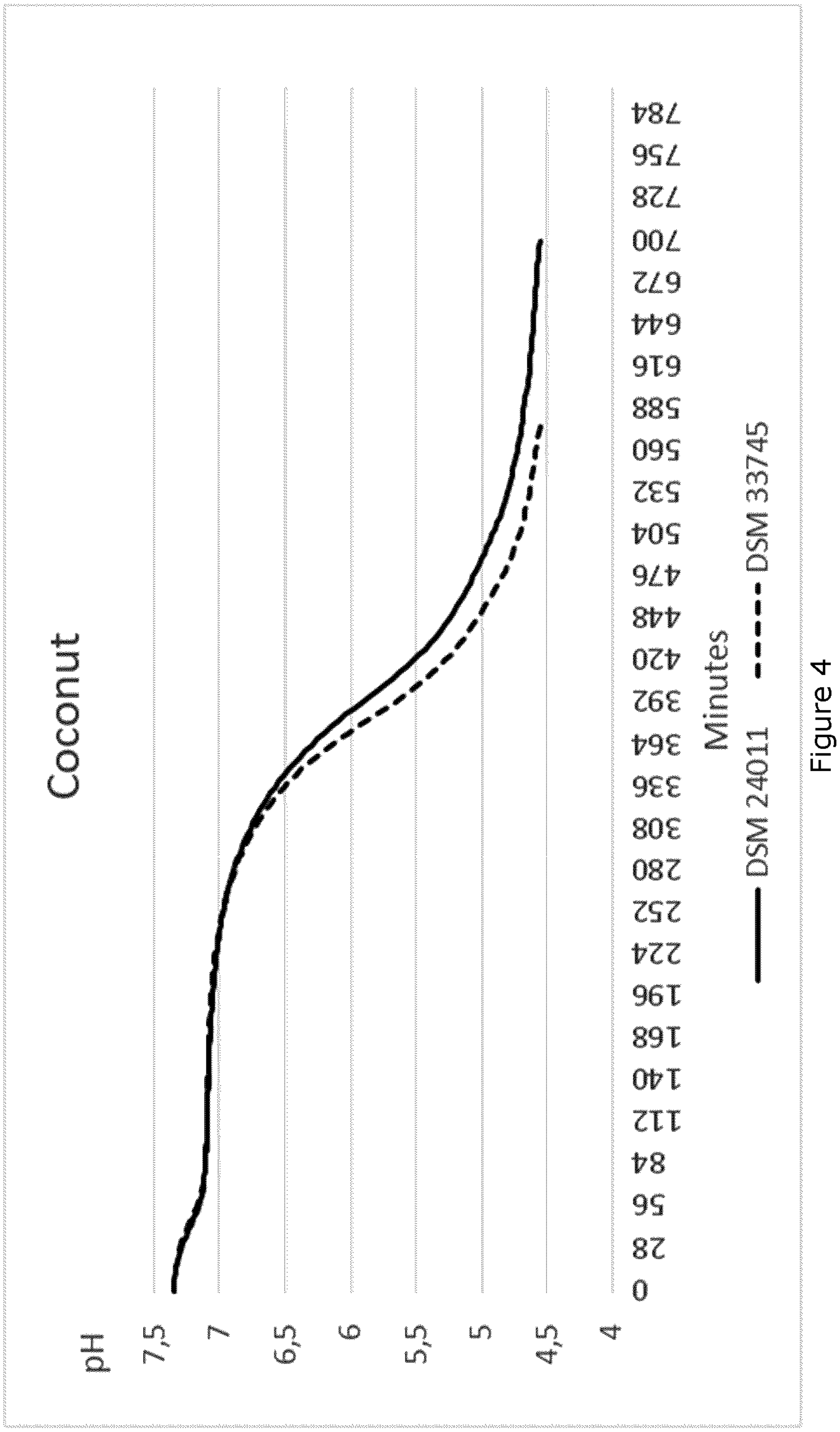
FIG. 4: Acidification profile of coconut base fermented with DSM 33745 and DSM 24011
Figure 5:
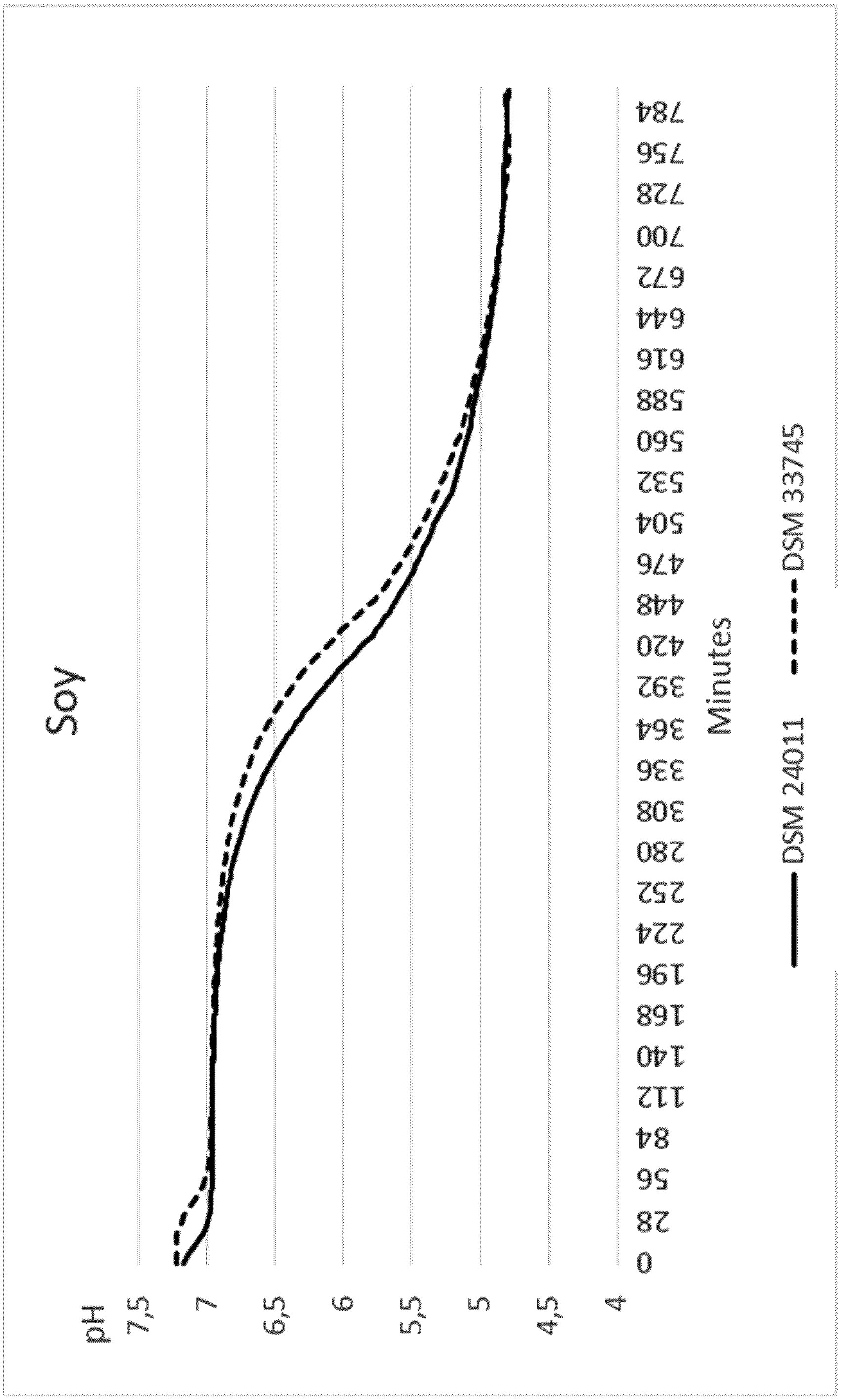
FIG. 5: Acidification profile of soy base fermented with DSM 33745 and DSM 24011

The results of the texture analysis are shown in the table below. In all plant bases, DSM 33745 develops texture to the same extent as DSM 24011 (shear stress at 300 1/s). In addition to the texture developed by this strain, DSM 33745 shows faster acidification in oat and in coconut bases compared to DSM 24011 (FIGS. 3 and 4), being respectively 13.5% and 17% faster (time to reaching pH 4.55). However, similar time is needed to reach pH 4.55, at the end of fermentation, in soy base for both strains (FIG. 5).

TABLE 14

Results of the texture analysis of the different plant-based samples, showing shear stress (Pa) at a shear rate of 300 1/s

| | Oat | Coconut | Soy |
|---|---|---|---|
| DSM 24011 | 23.3 | 92.7 | 52.4 |
| DSM 33745 | 26.1 | 93.8 | 54.8 |

Items:

Some items relates to:

Item Z1. A composition comprising (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) having a mutation in a gene of the ABC transporter operon, wherein said gene is selected from a group consisting of: ABC transporter sensor linked histidine kinase, ABC transporter sensor linked response regulator, and ABC transporter sensor and permease protein.

Item Z2. The composition according to item Z1, said composition comprising, either as a mixture or as a kit-of-parts, i) the *Streptococcus thermophilus* of item Z1(a) and/or (ii) the *Streptococcus thermophilus* of item Z1(b) and iii) at least one strain belonging to the species *Lactobacillus delbrueckii* subsp *bulgaricus* and/or *Lactobacillus acidophilus*.

Item Z3. The composition according to any one of item Z2, wherein:

the *Streptococcus thermophilus* strain of item Z1(a) is strain DSM 33118 or mutants or variants thereof and the *Streptococcus thermophilus* strain of item Z1(b) is selected from a group consisting of DSM 33745 or mutants or variants thereof, DSM 33746 or mutants or variants thereof, DSM 33747 or mutants or variants thereof and combinations thereof.

Item Z3a. The composition according to item Z1-Z2, wherein the *Lactobacillus delbrueckii* subsp *bulgaricus* strain is strain DSM 33571 or mutants or variants thereof.

Item Z4. The composition according to any one of items Z1-Z3, wherein the composition comprises *Streptococcus thermophilus* strains DSM 33118 and DSM 33745 and *Lactobacillus delbrueckii* subsp *bulgaricus* strain DSM 33571.

Item Z5. The composition according to any of items Z1-Z4, wherein the composition is a starter culture.

Item Z6. The composition according to any of items Z1-Z5, wherein the composition and/or starter culture is in frozen, spray-dried, freeze-dried, vacuum-dried, air dried, tray dried or liquid form.

Item Q1. A method of producing a dairy product, comprising fermenting a substrate with (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, or a composition according to any one of items Z1-Z6.

Item Q2. The method according to item Q1, wherein the substrate is a dairy substrate such as a milk substrate.

Item Q3. The method according to any one of items Q1-Q2, wherein the milk substrate is an animal derived product.

Item Q4. The method according to any one of items Q1-Q3, wherein the fermented product is a food product such as a dairy product.

Item Q5. The method according to items Q4, wherein the dairy product is selected from the group consisting of a fermented milk product (e.g. yoghurt, buttermilk or kefir) or a cheese (e.g. fresh cheese or pasta filata).

Item Q6. The method according to any one of items Q1-Q5, wherein the fermented product further comprises an ingredient selected from the group consisting of a fruit concentrate, a syrup, a probiotic bacterial strain or culture, a colouring agent, a thickening agent, a flavouring agent, a preserving agent and mixtures thereof.

Item Q7. The method according to any one of items Q1-Q6, wherein an enzyme is added to substrate before, during and/or after the fermenting, the enzyme being selected from the group consisting of an enzyme able to crosslink proteins, transglutaminase, an aspartic protease, chymosin, rennet and combinations thereof.

Item Q8. The method according to any one of items Q1-Q7, wherein the fermented product is in the form of a stirred type product, a set type product, or a drinkable product.

Item P1. A fermented product obtainable by the method according to any one of items Q1-Q8.

Item P2. The fermented product according to item P1, wherein the fermented product is a food product such as a dairy product.

Item T1. A fermented product comprising (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

Item T2. The fermented product according to item T1, wherein the fermented product is a dairy product.

Item W1. Use of (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein, for the manufacture of a fermented product.

Item W2. The use according to item W1, wherein the fermented product is a food product such as a dairy product.

Item X1. A *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1.

Item X2. The *Streptococcus thermophilus* strain according to any of the preceding claims, wherein the *Streptococcus thermophilus* strain is DSM 33118 or mutants or variants thereof.

Item X3. The *Streptococcus thermophilus* strain according to any one of the preceding claims, wherein the mutants and variants show the same or similar shear stress and/or gel firmness characteristics as DSM 33118.

Item X4. The *Streptococcus thermophilus* strain according to any one of the preceding claims, wherein said strain is galactose positive.

Item X5. The *Streptococcus thermophilus* strain according to any one of the preceding claims, wherein said strain is tellurite resistant.

Item Y1. A *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

Item Y2. A *Streptococcus thermophilus* strain according to Y1, wherein:
- the mutation in the ABC transporter sensor linked histidine kinase gene is a substitution of nucleotide T to nucleotide C in a position corresponding to position 692 in SEQ ID NO 2,
- the mutation in the ABC transporter sensor linked response regulator is a substitution of nucleotide T to nucleotide C in a position corresponding to position 530 in SEQ ID NO 3 or
- the mutation in the ABC transporter sensor and permease protein is a substitution of nucleotide T to nucleotide C in a position corresponding to position 1726 in SEQ ID NO 4.

Item Y3. A *Streptococcus thermophilus* strain according to Y1, wherein:
- the mutation in the ABC transporter sensor linked histidine kinase gene is a substitution of amino acid Leu to amino acid Ser in a position corresponding to 231 in SEQ ID NO 5,
- the mutation in the ABC transporter sensor linked response regulator is a substitution of amino acid Met to amino acid Thr in a position corresponding to 177 in SEQ ID NO 6,
- the mutation in the ABC transporter sensor and permease protein is a substitution of amino acid Phe to amino acid Leu in a position corresponding to 576 in the SEQ ID NO 7.

Item Y4. The *Streptococcus thermophilus* strain according to any of items Y1-Y3, wherein the *Streptococcus thermophilus* strain is selected from the group consisting of DSM 33745, DSM 33746 and DSM 33747 or mutants or variants thereof.

Item Y5. The *Streptococcus thermophilus* strain according to any of items Y1-Y4, wherein the mutants and variants show the same or similar shear stress and/or gel firmness characteristics as DSM 33745, DSM 33746 and DSM 33747.

Item Y6. The *Streptococcus thermophilus* strain according to any of items Y1-Y5, wherein said strain is bacitracin resistant.

Further items relates to:

Item A1. A composition comprising
- (a) a *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1, and/or
- (b) a *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

Item A2. The composition according to item A1, wherein
- the mutation in the ABC transporter sensor linked histidine kinase gene is in a position corresponding to position 231 in SEQ ID NO 5,
- the mutation in the ABC transporter sensor linked response regulator is in a position corresponding to position 177 in SEQ ID NO 6,
- the mutation in the ABC transporter sensor and permease protein is in a position corresponding to position 576 in the SEQ ID NO 7.

Item A3. The composition according to item A1 or item A2, wherein
- the mutation in the ABC transporter sensor linked histidine kinase gene is a substitution of amino acid Leu to amino acid Ser in a position corresponding to position 231 in SEQ ID NO 5,
- the mutation in the ABC transporter sensor linked response regulator is a substitution of amino acid Met to amino acid Thr in a position corresponding to position 177 in SEQ ID NO 6,
- the mutation in the ABC transporter sensor and permease protein is a substitution of amino acid Phe to amino acid Leu in a position corresponding to position 576 in the SEQ ID NO 7.

Item A4. The composition according to any one of the preceding items, wherein:
- the *Streptococcus thermophilus* strain of claim 1(a) is strain DSM 33118 or mutants or variants thereof and
- the *Streptococcus thermophilus* strain of claim 1(b) is selected from a group consisting of DSM 33745, DSM 33746 and DSM 33747 or mutants or variants thereof.

Item A5. The composition according to any one of the preceding claims, wherein the composition comprises one or more strain(s) belonging to the genus *Lactobacillus.*

Item A6. The composition according to any one of the preceding claims, wherein the composition comprises *Streptococcus thermophilus* strains DSM 33118 and DSM 33745 and *Lactobacillus delbrueckii* subsp *bulgaricus* strain DSM 33571.

Item 1B. A method of producing a fermented product comprising:
- fermenting a substrate with the *Streptococcus thermophilus* of item 1A(a) and/or the *Streptococcus thermophilus* of item 1A(b), or fermenting a substrate with the composition according to any one of items 1A-6A.

Item 1C. A fermented product obtainable by the method according to item 1B.

Item 1D. A fermented product comprising the *Streptococcus thermophilus* of item 1A(a) and/or (ii) the *Streptococcus thermophilus* of item 1A(b) or the composition according to any one of items 1A-6A.

Item 1E. Use of the *Streptococcus thermophilus* of item 1A(a) and/or (ii) the *Streptococcus thermophilus* of item 1A(b) for the manufacture of a fermented product or the composition according to any one of claims 1-6.

Item 1F. A *Streptococcus thermophilus* strain having a mutation in the −10-promotor box of the galactokinase (galK) gene, wherein said mutation is a substitution of nucleotide A to nucleotide C in a position corresponding to position 4 in SEQ ID NO 1.

Item 2F. The *Streptococcus thermophilus* strain according to item 1F, wherein the *Streptococcus thermophilus* strain is DSM 33118 or mutants or variants thereof.

Item 1G. A *Streptococcus thermophilus* strain having a mutation in a gene of the ABC transporter operon, wherein said gene is selected from a group consisting of: ABC transporter sensor linked histidine kinase, ABC transporter sensor linked response regulator, and ABC transporter sensor and permease protein.

Item 2G. A *Streptococcus thermophilus* strain according to item 1G, wherein:

the mutation in the ABC transporter sensor linked histidine kinase gene is in a position corresponding to position 231 in SEQ ID NO 5, the mutation in the ABC transporter sensor linked response regulator is in a position corresponding to position 177 in SEQ ID NO 6, the mutation in the ABC transporter sensor and permease protein is in a position corresponding to position 576 in the SEQ ID NO 7.

Item 3G. The *Streptococcus thermophilus* strain according to any of items 1G-2G, wherein the *Streptococcus thermophilus* strain is selected from the group consisting of DSM 33745, DSM 33746 and DSM 33747 or mutants or variants thereof.

SEQUENCE LISTING

SEQ ID NO 1: Promotor region of the galK gene—Nucleotide sequence

SEQ ID NO 2: ABC transporter sensor linked histidine kinase—Nucleotide sequence

SEQ ID NO 3: ABC transporter sensor linked response regulator—Nucleotide sequence SEQ ID NO 4: ABC transporter sensor and permease protein—Nucleotide sequence SEQ ID NO 5: ABC transporter sensor linked histidine kinase—Amino Acid sequence SEQ ID NO 6: ABC transporter sensor linked response regulator—Amino Acid sequence SEQ ID NO 7: ABC transporter sensor and permease protein—Amino Acid sequence

---

The invention claimed is:

1. A composition comprising one or both of:

(a) a *Streptococcus thermophilus* strain having a mutation in the −10-promotor box of the galactokinase (galK) gene, wherein said mutation is a substitution of nucleotide G to nucleotide A in a position corresponding to position 33 in SEQ ID NO: 1, wherein the strain is DSM 33118 or mutants or variants thereof; and (b) a *Streptococcus thermophilus* strain having a mutation in an ABC transporter operon gene selected from ABC transporter sensor linked histidine kinase, ABC transporter sensor linked response regulator, and ABC transporter sensor and permease protein.

2. The composition according to claim 1 comprising the *Streptococcus thermophilus* strain having a mutation in an ABC transporter operon gene, wherein:

the mutation in the ABC transporter sensor linked histidine kinase gene is in a position corresponding to position 231 in SEQ ID NO: 5, the mutation in the ABC transporter sensor linked response regulator is in a position corresponding to position 177 in SEQ ID NO: 6, and the mutation in the ABC transporter sensor and permease protein is in a position corresponding to position 576 in the SEQ ID: NO 7.

3. The composition according to claim 1 comprising the *Streptococcus thermophilus* strain having a mutation in an ABC transporter operon gene, wherein the mutation in the ABC transporter sensor linked histidine kinase gene is a substitution of amino acid Leu to amino acid Ser in a position corresponding to position 231 in SEQ ID NO: 5, the mutation in the ABC transporter sensor linked response regulator is a substitution of amino acid Met to amino acid Thr in a position corresponding to position 177 in SEQ ID NO: 6, and the mutation in the ABC transporter sensor and permease protein is a substitution of amino acid Phe to amino acid Leu in a position corresponding to position 576 in SEQ ID NO: 7.

4. The composition according to claim 1 comprising a *Streptococcus thermophilus* strain having a mutation in the ABC transporter operon gene, wherein said strain is one or more selected from DSM 33745, DSM 33746, DSM 33747, and mutants and variants thereof.

5. The composition according to claim 1, wherein the composition further comprises one or more strain(s) belonging to genus *Lactobacillus*.

6. The composition according to claim 5, wherein the composition comprises *Streptococcus thermophilus* strains DSM 33118 and DSM 33745 and *Lactobacillus delbrueckii* subsp *bulgaricus* strain DSM 33571.

* * * * *

SEQUENCE LISTING

```
<160> NUMBER OF SEQ ID NOS: 8

<210> SEQ ID NO 1
<211> LENGTH: 70
<212> TYPE: DNA
<213> ORGANISM: Streptococcus thermophilus
<220> FEATURE:
<223> OTHER INFORMATION: Promotor region of the galK gene

<400> SEQUENCE: 1

aaaatattga ttttccatgt gaaaggggtt acgatttcag tataaacaaa aagaataagt      60

gagatacatc                                                             70


<210> SEQ ID NO 2
<211> LENGTH: 975
<212> TYPE: DNA
<213> ORGANISM: Streptococcus thermophilus
<220> FEATURE:
<223> OTHER INFORMATION: ABC transporter sensor linked histidine kinase

<400> SEQUENCE: 2

atgatggata agcgtcaatt tatcacatat cagattaggt ctcgtctacc tttctatctt      60

ttgcttattt ttaatggaat catcttggtt ttgtttgctt ttttatttga agaggcagca     120

gatattcttc attatgcctt gaccatactg acatttgtgg ctatcatcat agttatttgg     180

gacttggtta gctcttatca gtcttataac ttagcctatc tctatgagaa aatgacacca     240

tcaagtcctt tagagtttta tctagctcag gccttggaaa atgctaagga gagtcaaatg     300

gttcagactg aggaggagcg caagcgctat acagatttga tggactacta taccctttgg     360

gtgcatcaaa tcaagacgcc aatagcagcc agtcaattat tgttagggga tgttacagat     420

agtaaaacga gggctctctt ggagcaagag gtcttcaaga ttgatgccta caccaatctg     480

gtcttgcagt atttacgttt ggaaaacttt catgatgatt tgcagttgag gcaggttgca     540
```

ttagacccct tggttaaaga agttattcga aagcatagtc ttttctttat tcaaaaaggg 600
ttgactatta acctagatga cctggatgtt aaggttattt cagatgaaaa atggctctta 660
gtcatcattg agcaggtctt gtcaaatagt ttgaagtaca caaagagtgg tggcattgac 720
atttacttta aagataatac gctttatctt aaagattctg ggattggtat caaggatagt 780
gatattttac gggtttttga gcgtggtttt tcaggttaca atggccgatt gactcagcag 840
tcgtctgggt taggtctcta tctttcaaag aaaattgctg atcagcttgg acatgatatt 900
agtattagct cccaagtagg tcaaggaacc acggtttcca ttcattttca aaagcagaag 960
ttggctattg attaa 975

<210> SEQ ID NO 3
<211> LENGTH: 681
<212> TYPE: DNA
<213> ORGANISM: Streptococcus thermophilus
<220> FEATURE:
<223> OTHER INFORMATION: ABC transporter sensor linked response regulator

<400> SEQUENCE: 3
atgcataaga ttttattagt tgaggacgac gaggttatcc gtcaacaagt caagaaaata 60
ctagaacagt gggagtacga agttgttctt gttgaagatt tcatggaagt attatctctt 120
tttgtaaaag aagaacccca cttggttctt atggatattg gtttacctct attcaacggt 180
tatcgctggt gtcaggaaat tcggaaggtc tccaaggtgc ctattatgtt cttgtcttcc 240
agagatcagg ccatggatat cgttatggca atcaatatgg gtggggacga ctttgtgact 300 aaacccttttg accaaaatgt tctcttggca aaaattcaag ggcttttgcg ccgatcttat 360
gagtttggaa aggatcagag tcttttggaa tatatgggtg tgattctgaa ccttaaggcc 420
atggatctgg tttatcaggg agaagtcgtt tctttgacta agaatgaatt tcagatttta 480
caagttctct ttgagcgttc tggtaatatc gttagtcgtg aagacctcat gaaggagctt 540
tggaatagtg acttctttat tgatgataac actctctctg taaatgtggc acgtttacgt 600
aagaagttag aggcagttgg tttgaaggac tttattgaaa ccaagaaagg tgtcggttac 660
gggttgcgtc atgatggata a 681

<210> SEQ ID NO 4
<211> LENGTH: 2001
<212> TYPE: DNA
<213> ORGANISM: Streptococcus thermophilus
<220> FEATURE:
<223> OTHER INFORMATION: ABC transporter sensor and permease protein

<400> SEQUENCE: 4
atgtttcgtc taaccaatag actggctttg tccaatctca taaaaaatcg taagctttat 60
tatccgtata cattggcaac tattctggtt attgctatta cctatatttt tacatcttta 120
acgcttaatt cgcatctgga tgacttaact ggggcagatg ctatcaagat ggttttgggg 180
ttgggacttg gaattgtcgc cctatcctct gggattattg ttctttatgc caacagcttt 240
gtcatgaaaa atcgttcaaa ggagcttggt ctctatagtg tgctaggctt ggagaagcgt 300
cacctcttta gtatgatttt aaaagaaacg atgattatgg gttttgtgac tttgcttcta 360
ggtataggtg taggggcgct attcgataaa ctcatttatg cttttcttca aaggattatc 420
ggtgaaggta ctggtttggt ttcgaccttt caagtaagga cgatccctat tgttcttgtc 480
atctttgctt gtatttttag tttgttggtt ttggtaaatg gtttccgatt actacggctt 540

```
aatcctttac aattaactaa agatggcctt aagggtgaga aaaaaggacg tttcctagtt    600
attcaaaccc ttttaggact tgggactatg ggatatggtt actatcttgc tctctctgtt    660
cagaatccag taacggctat tatcagtttt ttcctagctg ttttactggt cattttaggg    720
acttatcttc tcttcaacgc tgggacaaca gtagttctgc aactcttgaa aaagaagaaa    780
agctactatt acaagcctaa taatatgatt tccatttcca accttgtctt tcggatgaag    840
aaaaatgcag ttgggcttgc aaccattgct atcctctcaa gtatggttct cgtgacgctt    900
gtaggtgctg caagtatcta tgctggaaaa aaagactatc tggcgagtgc tgctccacat    960
gattacacag ttaccggaat gaatgtagat gtaacaagta cacaaaaggt tatggatgat   1020
ttcttatcac agtcgggaaa tcaggtcaat agaaaaacgg aagtaactta cctctacttt   1080
ggtatcaaag aacaagaaaa aaacaagcta accatctttt ctgagaatga aagaaaagtt   1140
ctaccaaagt cagtttttct tgtcttctca caagcaactt ataagcaatt aacaggtaaa   1200
gacctcaatc tgacttcaaa tcaagttagc ttatttacta aaaataaaat attgaaagat   1260
caaaagagtg tctctattaa tggtcaaaac taccagattc aggaaagcct taatgacttt   1320
attaaaggta aagtacctaa tatctttaca accatagttt ctgattatag ctaccttgtc   1380
gttcctgata tggatatttt taaagaaagt atcaaaggaa cagcaacaac tcaatctact   1440
tatgttggtg ttaacgtcaa agaccttaca catgaagcca agaaaaattc agatttgtta   1500
gacaaactca cggataaaga aatgcaacag ttagctggac aaactactgg tgtccctggg   1560
cctaacctca ctgctaatag ccgatatgat gtagaaggga tgctaaatgg ctttgttggc   1620
ggaaccttat ttatcggtat ttcttatcc attatcttta tgcttggcac agttctcgtg    1680
atttactata aacagatttc tgaaggttat gaggatcgtg agcgctttgt tattcttcaa   1740
aagattgggt tggacgacct tcaagtcaag caaaccattc gtaagcaagt tcttaccgtc   1800
ttcttcctcc ctttgatttt tgcctttatt cacttggcct ttgcttatca tatgatcagt   1860
ttgattgtgc gtatcattgg agttctcaat ccagatctta tgttagtggt tacaattatt   1920
gtttgtggcg ttttcttctt agcttatgtc ttggttttcg tcctaacgtc gcgttcttat   1980
cgtagaatcg tatcaatgta a                                             2001
```

<210> SEQ ID NO 5
<211> LENGTH: 324
<212> TYPE: PRT
<213> ORGANISM: Streptococcus thermophilus
<220> FEATURE:
<223> OTHER INFORMATION: ABC transporter sensor linked histidine kinase

<400> SEQUENCE: 5

```
Met Met Asp Lys Arg Gln Phe Ile Thr Tyr Gln Ile Arg Ser Arg Leu
1               5                   10                  15

Pro Phe Tyr Leu Leu Leu Ile Phe Asn Gly Ile Ile Leu Val Leu Phe
            20                  25                  30

Ala Phe Leu Phe Glu Glu Ala Ala Asp Ile Leu His Tyr Ala Leu Thr
        35                  40                  45

Ile Leu Thr Phe Val Ala Ile Ile Ile Val Ile Trp Asp Leu Val Ser
    50                  55                  60

Ser Tyr Gln Ser Tyr Asn Leu Ala Tyr Leu Tyr Glu Lys Met Thr Pro
65                  70                  75                  80

Ser Ser Pro Leu Glu Phe Tyr Leu Ala Gln Ala Leu Glu Asn Ala Lys
                85                  90                  95
```

Glu Ser Gln Met Val Gln Thr Glu Glu Glu Arg Lys Arg Tyr Thr Asp
100 105 110

Leu Met Asp Tyr Tyr Thr Leu Trp Val His Gln Ile Lys Thr Pro Ile
115 120 125

Ala Ala Ser Gln Leu Leu Leu Gly Asp Val Thr Asp Ser Lys Thr Arg
130 135 140

Ala Leu Leu Glu Gln Glu Val Phe Lys Ile Asp Ala Tyr Thr Asn Leu
145 150 155 160

Val Leu Gln Tyr Leu Arg Leu Glu Asn Phe His Asp Asp Leu Gln Leu
165 170 175

Arg Gln Val Ala Leu Asp Pro Leu Val Lys Glu Val Ile Arg Lys His
180 185 190

Ser Leu Phe Phe Ile Gln Lys Gly Leu Thr Ile Asn Leu Asp Asp Leu
195 200 205

Asp Val Lys Val Ile Ser Asp Glu Lys Trp Leu Leu Val Ile Ile Glu
210 215 220

Gln Val Leu Ser Asn Ser Leu Lys Tyr Thr Lys Ser Gly Gly Ile Asp
225 230 235 240

Ile Tyr Phe Lys Asp Asn Thr Leu Tyr Leu Lys Asp Ser Gly Ile Gly
245 250 255

Ile Lys Asp Ser Asp Ile Leu Arg Val Phe Glu Arg Gly Phe Ser Gly
260 265 270

Tyr Asn Gly Arg Leu Thr Gln Gln Ser Ser Gly Leu Gly Leu Tyr Leu
275 280 285

Ser Lys Lys Ile Ala Asp Gln Leu Gly His Asp Ile Ser Ile Ser Ser
290 295 300

Gln Val Gly Gln Gly Thr Thr Val Ser Ile His Phe Gln Lys Gln Lys
305 310 315 320

Leu Ala Ile Asp

<210> SEQ ID NO 6
<211> LENGTH: 226
<212> TYPE: PRT
<213> ORGANISM: Streptococcus thermophilus
<220> FEATURE:
<223> OTHER INFORMATION: ABC transporter sensor linked response regulator

<400> SEQUENCE: 6

Met His Lys Ile Leu Leu Val Glu Asp Asp Glu Val Ile Arg Gln Gln
1 5 10 15

Val Lys Lys Ile Leu Glu Gln Trp Glu Tyr Glu Val Val Leu Val Glu
20 25 30

Asp Phe Met Glu Val Leu Ser Leu Phe Val Lys Glu Glu Pro His Leu
35 40 45

Val Leu Met Asp Ile Gly Leu Pro Leu Phe Asn Gly Tyr Arg Trp Cys
50 55 60

Gln Glu Ile Arg Lys Val Ser Lys Val Pro Ile Met Phe Leu Ser Ser
65 70 75 80

Arg Asp Gln Ala Met Asp Ile Val Met Ala Ile Asn Met Gly Gly Asp
85 90 95

Asp Phe Val Thr Lys Pro Phe Asp Gln Asn Val Leu Leu Ala Lys Ile
100 105 110

Gln Gly Leu Leu Arg Arg Ser Tyr Glu Phe Gly Lys Asp Gln Ser Leu
115 120 125

```
Leu Glu Tyr Met Gly Val Ile Leu Asn Leu Lys Ala Met Asp Leu Val
    130                 135                 140

Tyr Gln Gly Glu Val Val Ser Leu Thr Lys Asn Glu Phe Gln Ile Leu
145                 150                 155                 160

Gln Val Leu Phe Glu Arg Ser Gly Asn Ile Val Ser Arg Glu Asp Leu
                165                 170                 175

Met Lys Glu Leu Trp Asn Ser Asp Phe Phe Ile Asp Asp Asn Thr Leu
            180                 185                 190

Ser Val Asn Val Ala Arg Leu Arg Lys Lys Leu Glu Ala Val Gly Leu
        195                 200                 205

Lys Asp Phe Ile Glu Thr Lys Lys Gly Val Gly Tyr Gly Leu Arg His
    210                 215                 220

Asp Gly
225


<210> SEQ ID NO 7
<211> LENGTH: 666
<212> TYPE: PRT
<213> ORGANISM: Streptococcus thermophilus
<220> FEATURE:
<223> OTHER INFORMATION: ABC transporter sensor and permease protein

<400> SEQUENCE: 7

Met Phe Arg Leu Thr Asn Arg Leu Ala Leu Ser Asn Leu Ile Lys Asn
1               5                   10                  15

Arg Lys Leu Tyr Tyr Pro Tyr Thr Leu Ala Thr Ile Leu Val Ile Ala
            20                  25                  30

Ile Thr Tyr Ile Phe Thr Ser Leu Thr Leu Asn Ser His Leu Asp Asp
        35                  40                  45

Leu Thr Gly Ala Asp Ala Ile Lys Met Val Leu Gly Leu Gly Leu Gly
    50                  55                  60

Ile Val Ala Leu Ser Ser Gly Ile Ile Val Leu Tyr Ala Asn Ser Phe
65                  70                  75                  80

Val Met Lys Asn Arg Ser Lys Glu Leu Gly Leu Tyr Ser Val Leu Gly
                85                  90                  95

Leu Glu Lys Arg His Leu Phe Ser Met Ile Leu Lys Glu Thr Met Ile
            100                 105                 110

Met Gly Phe Val Thr Leu Leu Leu Gly Ile Gly Val Gly Ala Leu Phe
        115                 120                 125

Asp Lys Leu Ile Tyr Ala Phe Leu Gln Arg Ile Ile Gly Glu Gly Thr
    130                 135                 140

Gly Leu Val Ser Thr Phe Gln Val Arg Thr Ile Pro Ile Val Leu Val
145                 150                 155                 160

Ile Phe Ala Cys Ile Phe Ser Leu Leu Val Leu Val Asn Gly Phe Arg
                165                 170                 175

Leu Leu Arg Leu Asn Pro Leu Gln Leu Thr Lys Asp Gly Leu Lys Gly
            180                 185                 190

Glu Lys Lys Gly Arg Phe Leu Val Ile Gln Thr Leu Leu Gly Leu Gly
        195                 200                 205

Thr Met Gly Tyr Gly Tyr Tyr Leu Ala Leu Ser Val Gln Asn Pro Val
    210                 215                 220

Thr Ala Ile Ile Ser Phe Phe Leu Ala Val Leu Leu Val Ile Leu Gly
225                 230                 235                 240

Thr Tyr Leu Leu Phe Asn Ala Gly Thr Thr Val Val Leu Gln Leu Leu
                245                 250                 255
```

-continued

```
Lys Lys Lys Lys Ser Tyr Tyr Tyr Lys Pro Asn Asn Met Ile Ser Ile
            260                 265                 270

Ser Asn Leu Val Phe Arg Met Lys Lys Asn Ala Val Gly Leu Ala Thr
        275                 280                 285

Ile Ala Ile Leu Ser Ser Met Val Leu Val Thr Leu Val Gly Ala Ala
    290                 295                 300

Ser Ile Tyr Ala Gly Lys Lys Asp Tyr Leu Ala Ser Ala Ala Pro His
305                 310                 315                 320

Asp Tyr Thr Val Thr Gly Met Asn Val Asp Val Thr Ser Thr Gln Lys
                325                 330                 335

Val Met Asp Asp Phe Leu Ser Gln Ser Gly Asn Gln Val Asn Arg Lys
            340                 345                 350

Thr Glu Val Thr Tyr Leu Tyr Phe Gly Ile Lys Glu Gln Glu Lys Asn
        355                 360                 365

Lys Leu Thr Ile Phe Ser Glu Asn Glu Arg Lys Val Leu Pro Lys Ser
    370                 375                 380

Val Phe Leu Val Phe Ser Gln Ala Thr Tyr Lys Gln Leu Thr Gly Lys
385                 390                 395                 400

Asp Leu Asn Leu Thr Ser Asn Gln Val Ser Leu Phe Thr Lys Asn Lys
                405                 410                 415

Ile Leu Lys Asp Gln Lys Ser Val Ser Ile Asn Gly Gln Asn Tyr Gln
            420                 425                 430

Ile Gln Glu Ser Leu Asn Asp Phe Ile Lys Gly Lys Val Pro Asn Ile
        435                 440                 445

Phe Thr Thr Ile Val Ser Asp Tyr Ser Tyr Leu Val Val Pro Asp Met
    450                 455                 460

Asp Ile Phe Lys Glu Ser Ile Lys Gly Thr Ala Thr Thr Gln Ser Thr
465                 470                 475                 480

Tyr Val Gly Val Asn Val Lys Asp Leu Thr His Glu Ala Lys Lys Asn
                485                 490                 495

Ser Asp Leu Leu Asp Lys Leu Thr Asp Lys Glu Met Gln Gln Leu Ala
            500                 505                 510

Gly Gln Thr Thr Gly Val Pro Gly Pro Asn Leu Thr Ala Asn Ser Arg
        515                 520                 525

Tyr Asp Val Glu Gly Met Leu Asn Gly Phe Val Gly Gly Thr Leu Phe
    530                 535                 540

Ile Gly Ile Phe Leu Ser Ile Ile Phe Met Leu Gly Thr Val Leu Val
545                 550                 555                 560

Ile Tyr Tyr Lys Gln Ile Ser Glu Gly Tyr Glu Asp Arg Glu Arg Phe
                565                 570                 575

Val Ile Leu Gln Lys Ile Gly Leu Asp Asp Leu Gln Val Lys Gln Thr
            580                 585                 590

Ile Arg Lys Gln Val Leu Thr Val Phe Phe Leu Pro Leu Ile Phe Ala
        595                 600                 605

Phe Ile His Leu Ala Phe Ala Tyr His Met Ile Ser Leu Ile Val Arg
    610                 615                 620

Ile Ile Gly Val Leu Asn Pro Asp Leu Met Leu Val Val Thr Ile Ile
625                 630                 635                 640

Val Cys Gly Val Phe Phe Leu Ala Tyr Val Leu Val Phe Val Leu Thr
                645                 650                 655

Ser Arg Ser Tyr Arg Arg Ile Val Ser Met
            660                 665
```

-continued

```
<210> SEQ ID NO 8
<211> LENGTH: 70
<212> TYPE: DNA
<213> ORGANISM: Streptococcus thermophilus
<220> FEATURE:
<223> OTHER INFORMATION: Promotor region of the galK gene of DSM 33118

<400> SEQUENCE: 8

aaaatattga ttttccatgt gaaaggggtt acaatttcag tataaacaaa aagaataagt     60

gagatacatc                                                            70
```